(12) United States Patent  (10) Patent No.: US 11,497,394 B2
Molnar                     (45) Date of Patent:     Nov. 15, 2022

(54) LARYNGOSCOPE AND INTUBATION METHODS

(71) Applicant: WM & DG, Inc., Deerfield, IL (US)

(72) Inventor: Robert W. Molnar, Long Grove, IL (US)

(73) Assignee: WM & DG, INC., Deerfield, IL (US)

( * ) Notice: Subject to any disclaimer, the term of this patent is extended or adjusted under 35 U.S.C. 154(b) by 0 days.

(21) Appl. No.: 17/215,521

(22) Filed: Mar. 29, 2021

(65) Prior Publication Data

US 2022/0110514 A1  Apr. 14, 2022

Related U.S. Application Data

(60) Provisional application No. 63/090,560, filed on Oct. 12, 2020.

(51) Int. Cl.
| | |
|---|---|
| *A61B 1/267* | (2006.01) |
| *A61B 1/00* | (2006.01) |
| *A61B 1/05* | (2006.01) |
| *A61B 1/018* | (2006.01) |
| *A61M 16/04* | (2006.01) |

(52) U.S. Cl.
CPC .......... *A61B 1/267* (2013.01); *A61B 1/00073* (2013.01); *A61B 1/00082* (2013.01); *A61B 1/00094* (2013.01); *A61B 1/018* (2013.01); *A61B 1/05* (2013.01); *A61M 16/0434* (2013.01); *A61M 16/0486* (2014.02); *A61M 16/0488* (2013.01)

(58) Field of Classification Search
CPC ...... A61B 1/267; A61B 1/018; A61B 1/00073
See application file for complete search history.

(56) References Cited

U.S. PATENT DOCUMENTS

| | | |
|---|---|---|
| 4,231,365 A | 11/1980 | Scarberry |
| 4,360,008 A | 11/1982 | Corazzelli, Jr. |
| 4,577,638 A | 3/1986 | Graham |
| 4,584,998 A | 4/1986 | McGrail |
| 4,607,643 A | 8/1986 | Bell et al. |
| 4,846,153 A | 7/1989 | Berci |

(Continued)

FOREIGN PATENT DOCUMENTS

| | | |
|---|---|---|
| CN | 204484044 U | 7/2015 |
| EP | 0665029 A2 | 8/1995 |

(Continued)

OTHER PUBLICATIONS

Bledsoe B., "The Disappearing Endotrachael Tube"., Clinical Professor of Emergency Medicine, University of Nevada School of Medicine, 2009, 84 pages.

(Continued)

*Primary Examiner* — Matthew J Kasztejna
(74) *Attorney, Agent, or Firm* — Greer, Burns & Cain, Ltd.

(57) ABSTRACT

In one aspect, this disclosure relates to a laryngoscope having a channel for delivering an endotracheal tube to the trachea and its placement under continuous visualization by a camera and with controlled suction. The laryngoscope may further comprise one or more additional channels, including a suction and camera channel. In another aspect, this disclosure relates to medical systems comprising one of laryngoscopes according to this disclosure and one or more of adapters, tools and/or cameras.

17 Claims, 19 Drawing Sheets

(56) References Cited

U.S. PATENT DOCUMENTS

| | | |
|---|---|---|
| 5,052,386 A | 1/1991 | Fischer, Jr. |
| 5,025,778 A | 6/1991 | Silverstein et al. |
| 5,174,283 A | 12/1992 | Parker |
| 5,193,692 A | 3/1993 | Farley et al. |
| 5,203,320 A * | 4/1993 | Augustine ......... A61M 16/0488 |
| | | 128/200.26 |
| 5,241,956 A | 9/1993 | Brain |
| 5,287,848 A * | 2/1994 | Cubb ................ A61M 16/0488 |
| | | 128/200.26 |
| 5,353,787 A | 10/1994 | Price |
| 5,372,131 A | 12/1994 | Heinen, Jr. |
| 5,400,771 A | 3/1995 | Pirak et al. |
| 5,499,625 A | 3/1996 | Frass et al. |
| 5,511,916 A | 4/1996 | Farley et al. |
| 5,513,627 A | 5/1996 | Flam |
| 5,515,844 A | 5/1996 | Christopher |
| 5,551,947 A | 9/1996 | Kaali |
| 5,632,271 A | 5/1997 | Brain |
| 5,665,052 A | 9/1997 | Bullard |
| 5,682,880 A | 11/1997 | Brain |
| 5,733,242 A | 3/1998 | Raybum et al. |
| 5,740,791 A | 4/1998 | Aves |
| 5,819,733 A | 10/1998 | Bertram |
| 5,845,634 A * | 12/1998 | Parker ..................... A61B 1/07 |
| | | 128/200.26 |
| 5,879,306 A | 3/1999 | Fontenot et al. |
| 5,888,195 A | 3/1999 | Schneider |
| 6,038,629 A | 3/2000 | Ogilvie et al. |
| 6,115,523 A | 9/2000 | Choi et al. |
| 6,142,144 A | 11/2000 | Pacey |
| 6,189,533 B1 | 2/2001 | Simon et al. |
| 6,196,225 B1 | 3/2001 | Allgeyer |
| 6,248,061 B1 | 12/2001 | Cook, Jr. |
| 6,349,720 B1 | 2/2002 | Clark |
| 6,386,199 B1 | 5/2002 | Alfery |
| 6,439,232 B1 | 8/2002 | Brain |
| 6,440,061 B1 | 8/2002 | Wenner et al. |
| 6,443,156 B1 | 9/2002 | Niklason et al. |
| 6,527,704 B1 | 3/2003 | Chang et al. |
| 6,543,447 B2 | 4/2003 | Pacey |
| 6,626,169 B2 | 9/2003 | Gaitini |
| 6,631,720 B1 | 10/2003 | Brain |
| 6,634,354 B2 | 10/2003 | Christopher |
| 6,655,377 B2 | 12/2003 | Pacey |
| 6,677,990 B1 | 1/2004 | Kawahara |
| 6,860,264 B2 | 3/2005 | Christopher |
| 6,860,270 B2 | 3/2005 | Sniadach |
| 6,918,391 B1 | 7/2005 | Moore |
| 7,052,456 B2 | 5/2006 | Simon |
| 7,128,509 B2 | 10/2006 | Farley et al. |
| 7,156,091 B2 | 1/2007 | Koyama et al. |
| 7,237,993 B2 | 7/2007 | Farley et al. |
| 7,331,925 B2 | 2/2008 | McMorrow et al. |
| 7,421,877 B2 | 9/2008 | Frenken |
| 7,450,746 B2 | 11/2008 | Yang et al. |
| 7,493,901 B2 | 2/2009 | Brain |
| 7,520,857 B2 | 4/2009 | Chalana et al. |
| 7,527,601 B2 | 5/2009 | Dubey et al. |
| 7,611,466 B2 | 11/2009 | Chalana et al. |
| 7,654,970 B2 | 2/2010 | Dubey |
| D611,138 S | 3/2010 | Nasir |
| D615,188 S | 3/2010 | Nasir |
| 7,713,189 B2 | 5/2010 | Hanke |
| 7,713,216 B2 | 5/2010 | Dubey et al. |
| 7,727,150 B2 | 6/2010 | Chalana et al. |
| 7,744,534 B2 | 6/2010 | Chalana et al. |
| 7,749,165 B2 | 7/2010 | McMorrow et al. |
| 7,749,176 B2 | 7/2010 | Dubey |
| 7,806,119 B2 | 10/2010 | Nasir |
| 7,811,239 B2 | 10/2010 | Dubey et al. |
| 7,819,806 B2 | 10/2010 | Yang et al. |
| 7,854,324 B2 | 12/2010 | Farley et al. |
| 7,896,007 B2 | 3/2011 | Brain |
| 7,921,847 B2 | 4/2011 | Totz |
| 7,942,813 B2 | 5/2011 | Mackin |
| 7,976,458 B2 | 7/2011 | Stefanchik et al. |
| 8,016,760 B2 | 9/2011 | Chalana et al. |
| 8,038,629 B2 | 10/2011 | Solanki et al. |
| 8,202,215 B2 | 6/2012 | Xiao et al. |
| 8,215,307 B2 | 7/2012 | Nasir |
| 8,297,275 B2 | 10/2012 | Ogilvie et al. |
| 8,308,644 B2 | 11/2012 | McMorrow et al. |
| 8,371,303 B2 | 2/2013 | Schaner et al. |
| 8,529,442 B2 | 9/2013 | Pacey et al. |
| 8,863,746 B2 | 10/2014 | Totz |
| 8,928,746 B1 | 1/2015 | Stevrin et al. |
| 9,211,060 B2 | 12/2015 | Waldron et al. |
| 9,415,179 B2 | 8/2016 | Molnar |
| 9,427,142 B2 | 8/2016 | Terliuc |
| 9,579,012 B2 | 2/2017 | Vazales et al. |
| 9,820,642 B2 * | 11/2017 | Law .................. A61M 16/0488 |
| 9,833,587 B2 | 12/2017 | Cook |
| 10,213,567 B1 | 2/2019 | Theventhiran |
| 10,342,944 B2 | 7/2019 | Molnar |
| 2002/0108610 A1 | 8/2002 | Christopher |
| 2002/0195103 A1 | 12/2002 | O'Mara |
| 2003/0220542 A1 | 11/2003 | Belson et al. |
| 2004/0230136 A1 | 11/2004 | Corrigan, Jr. |
| 2004/0258249 A1 | 12/2004 | Niederdrank et al. |
| 2005/0090712 A1 * | 4/2005 | Cubb .................. A61B 1/00195 |
| | | 600/120 |
| 2005/0054903 A1 | 5/2005 | Cantrell |
| 2005/0182297 A1 | 8/2005 | Gravenstein et al. |
| 2005/0228226 A1 | 10/2005 | Muckner |
| 2005/0244801 A1 | 11/2005 | DeSalvo |
| 2005/0268917 A1 | 12/2005 | Boedeker et al. |
| 2006/0004260 A1 | 1/2006 | Boedeker et al. |
| 2006/0032505 A1 | 2/2006 | Alfery et al. |
| 2006/0111633 A1 | 5/2006 | McMorrow et al. |
| 2006/0149129 A1 | 7/2006 | Watts et al. |
| 2006/0162730 A1 | 7/2006 | Glassenberg et al. |
| 2006/0167375 A1 | 7/2006 | Terrassse et al. |
| 2006/0180155 A1 | 8/2006 | Glassenberg et al. |
| 2006/0276694 A1 | 12/2006 | Acha Gandarias |
| 2007/0095351 A1 | 5/2007 | Globel |
| 2007/0106121 A1 | 5/2007 | Yokota et al. |
| 2007/0137651 A1 | 7/2007 | Glassenberg et al. |
| 2007/0156068 A1 | 7/2007 | Dubey |
| 2007/0175482 A1 | 8/2007 | Kimmel et al. |
| 2007/0180887 A1 | 8/2007 | Frenken |
| 2007/0203393 A1 | 8/2007 | Stefanchik |
| 2007/0239197 A1 | 10/2007 | Dubey |
| 2007/0255185 A1 | 11/2007 | Dubey |
| 2008/0029100 A1 | 2/2008 | Glassenberg et al. |
| 2008/0076989 A1 | 3/2008 | Hete et al. |
| 2008/0114268 A1 | 5/2008 | Dubey |
| 2008/0115783 A1 | 5/2008 | Brain |
| 2008/0146879 A1 | 6/2008 | Pacey |
| 2008/0188774 A1 | 8/2008 | Dubey |
| 2008/0221391 A1 | 9/2008 | Weitzner et al. |
| 2008/0276932 A1 | 11/2008 | Bassoul |
| 2008/0287834 A1 | 11/2008 | Pusch |
| 2009/0003201 A1 | 2/2009 | Law et al. |
| 2009/0088596 A1 | 4/2009 | Yaegashi |
| 2009/0090356 A1 | 4/2009 | Cook |
| 2009/0105600 A1 | 4/2009 | Marks et al. |
| 2009/0177044 A1 | 7/2009 | Cohen et al. |
| 2009/0194102 A1 | 8/2009 | Chen et al. |
| 2009/0194114 A1 | 8/2009 | Chen et al. |
| 2009/0227835 A1 | 9/2009 | Terliuc |
| 2010/0051024 A1 | 3/2010 | Abrons |
| 2010/0056879 A1 | 3/2010 | Greenspan et al. |
| 2010/0056906 A1 | 3/2010 | Van Der Brug |
| 2010/0113916 A1 | 5/2010 | Kumar |
| 2010/0147309 A1 | 6/2010 | Cuevas et al. |
| 2010/0204546 A1 | 8/2010 | Hassidov et al. |
| 2010/0249639 A1 | 9/2010 | Bhatt |
| 2010/0261967 A1 | 10/2010 | Pacey et al. |
| 2010/0312069 A1 | 12/2010 | Sutherland et al. |
| 2011/0030694 A1 | 2/2011 | Schaner et al. |
| 2011/0130632 A1 | 6/2011 | McGrail et al. |
| 2011/0137127 A1 | 6/2011 | Schwartz et al. |
| 2011/0178372 A1 | 6/2011 | Pacey et al. |
| 2011/0201882 A1 | 8/2011 | Schwartz et al. |

(56) References Cited

U.S. PATENT DOCUMENTS

| | | |
|---|---|---|
| 2011/0315147 A1 | 12/2011 | Wood et al. |
| 2012/0059223 A1 | 3/2012 | McGrath et al. |
| 2012/0259173 A1 | 10/2012 | Waldron et al. |
| 2012/0260921 A1 | 10/2012 | Sangwan |
| 2012/0302833 A1 | 11/2012 | Hayman et al. |
| 2013/0006051 A1 | 1/2013 | Stace et al. |
| 2013/0030249 A1 | 1/2013 | Vazales et al. |
| 2013/0096379 A1 | 4/2013 | Golbert |
| 2013/0109918 A1 | 5/2013 | Pagan |
| 2013/0158351 A1 | 6/2013 | Daher et al. |
| 2013/0197303 A1 | 8/2013 | Chun |
| 2013/0253368 A1 | 9/2013 | Are et al. |
| 2013/0324798 A1 | 12/2013 | Molnar et al. |
| 2014/0018626 A1 | 1/2014 | Lee |
| 2014/0073853 A1 | 3/2014 | Swisher et al. |
| 2014/0076309 A1 | 3/2014 | Takeda |
| 2014/0096766 A1 | 4/2014 | Avitsian |
| 2014/0166020 A1 | 6/2014 | Chang |
| 2014/0194694 A1 | 7/2014 | Chen |
| 2014/0323806 A1 | 10/2014 | Brain |
| 2014/0338826 A1 | 11/2014 | Nasir |
| 2014/0357951 A1 | 12/2014 | Muller et al. |
| 2015/0122251 A1 | 5/2015 | Azhir et al. |
| 2016/0038008 A1 | 2/2016 | Molnar |
| 2016/0038014 A1 | 2/2016 | Molnar |
| 2016/0262603 A1 | 9/2016 | Molnar |
| 2016/0317768 A1 | 11/2016 | Nasir et al. |
| 2016/0331918 A1 | 11/2016 | Nasir et al. |
| 2016/0345803 A1 | 12/2016 | Mallory et al. |
| 2016/0346493 A1 | 12/2016 | Wight |
| 2017/0072154 A1 | 3/2017 | Hoftman et al. |
| 2017/0196445 A1 | 7/2017 | Gardner |
| 2017/0209022 A1 | 7/2017 | Molnar |
| 2017/0216544 A1 | 8/2017 | Baska |
| 2018/0104427 A1 | 4/2018 | Avitsian |
| 2018/0169365 A1 | 6/2018 | Sawyer |
| 2019/0059710 A1 | 2/2019 | Molnar |
| 2020/0113427 A1 | 4/2020 | Molnar |

FOREIGN PATENT DOCUMENTS

| | | |
|---|---|---|
| KR | 20120095385 | 8/2012 |
| WO | WO9405200 | 3/1994 |
| WO | 03/084719 A2 | 10/2003 |
| WO | 2003084719 | 10/2003 |
| WO | 2008123934 A1 | 10/2008 |
| WO | 2009025843 A1 | 2/2009 |
| WO | WO2010120950 | 10/2010 |
| WO | 2012/080293 A2 | 6/2012 |
| WO | 2013/017535 A2 | 2/2013 |
| WO | 2015013172 | 1/2015 |
| WO | WO2016022759 A1 | 2/2016 |

OTHER PUBLICATIONS

Bledso B., "Incubation Threatened by New Devices and Lack of Paramedic Practice", Patient Care, Jems.com; http://www.jems.com/article/patient-care/incubation-threatened-new-devi, printed Feb. 21, 2015, 8 pages.

Bledso B., "Incubation Threatened by New Devices and Lack of Paramedic Practice", Patient Care; http://www.jems.com/article/patient-care/intubation-threatened-new-devi, printed Mar. 20, 2015, 14 pages.

Naik et al., "Intubation Success through I-Gel® and Intubating Laryngeal Mask Airway® Using Flexible Silicone Tubes: A Randomised Noninferiority Trial", Anesthesiology Research and Practice, 2016, pp. 1-8.

Genzwuerker, MD. et al. "Laryngeal tube: a review of current literature" AJA-Online.com 2011:vol. 12, p. 22-33.

Kodali MD, "Capnography in emergency medicine—911" http://www.capnography.com/outside/922.htm., printed Feb. 21, 2015, 9 pages.

ETView Medical, Ltd., Announces the Appointment of David Amar, MD to Its Scientific Advisory Board, 2012; http://finance.yahoo.com/news/etview-medical-ltd-announces-appointment-104300770.html, Jun. 4, 2012, 3 pages.

ETVIEW, "VivaSight-DL disposable dual lumen airway ventilation tube with integrated high resolution airway imaging system permitting airway control and lung isolation", http://www.etview.com/index_old.php, Jun. 21, 2012. 1 page.

Kapoor et al., "Comparison of supraglottic devices i-gel® and LMA Fastrach® as conduit for endotracheal intubation", Indian Journal of Anaesthesia, Jul. 2014-Aug., pp. 397-402, vol. 58(4).

"How to Use a Jem Endotrachael Tube Changer," Endotrachael Tube Changers, Instrumentatio Industries, Inc., Bethal Park, PA, 2015, 2 pages.

ETView Medical Ltd., "ETView Medical, Ltd., Announces Exclusive Patent License Agreement—Feb. 2, 2012", http://worldnetdaily.com.uk/markets/news/read/20671060/etview_medical, Jul. 5, 2012, 3 pages.

PCT Search Report dated Jan. 12, 2022 for related PCT Application No. PCT/US2021/054478.

\* cited by examiner

LARYNGOSCOPE AND INTUBATION METHODS

CROSS-REFERENCE TO RELATED APPLICATIONS

This application claims the benefit of priority to U.S. provisional patent application 63/090,560 filed Oct. 12, 2020, the entire disclosure of which is herein incorporated in its entirety by the reference.

TECHNICAL FIELD

This disclosure relates to the field of medical devices, including medical devices for managing a patient airway and intubation methods, including laryngoscopes containing a channel for delivering and positioning an endotracheal tube under continuous visualization, at least one camera/suction channel and/or at least one camera/tool channel.

BACKGROUND

A healthcare professional may use a laryngoscope for gaining access to patient's airway in medical emergency, e.g., a facial trauma, and/or in order to facilitate endotracheal intubation during certain surgical procedures, in general anesthesia and/or under other circumstances when a patient cannot breathe unassisted. Laryngoscopes known in the art comprise a handle attached to a blade. A healthcare professional may insert the blade into the oropharynx by manipulating the handle in order to obtain a view of the vocal cords and the glottis and while attempting to gain access to an airway and further in order to keep the airway accessible in order to position an endotracheal tube or some other airway device which will facilitate breathing and/or deliver a medication.

For proper placement of an endotracheal tube and in order to establish ventilation, it is particularly important for a healthcare professional to view the patient's larynx, including vocal cords. However, the airway may be obstructed with vomit, blood, and/or some other bodily secretion. A healthcare professional may use a suction tube in order to aspirate these bodily secretions. Various attempts have been made to combine a laryngoscope with a suction tube, including a suctioning laryngoscope blade to which a suction tube is coupled, as provided in U.S. Pat. No. 6,248,061 or a laryngoscope with integrated and controllable suction, as disclosed in US Patent Publication 2016/0345803.

Various attempts have been also made for adopting a blade of a laryngoscope to delivering an endotracheal tube. For example, U.S. Pat. No. 8,529,442 provides laryngoscopes having an external centrally located channel. For proper placement of an endotracheal tube and in order to establish ventilation, it is particularly important for a healthcare professional to view the patient's larynx, including vocal cords. Certain video laryngoscopes are known in the art, including U.S. Pat. No. 8,529,442 disclosing a video laryngoscope including a camera and lighting unit located beneath the external channel.

However, there remains a need in the field for a laryngoscope capable of assisting in accurate and expeditious placement of an endotracheal tube.

SUMMARY

This disclosure helps in addressing the need in the field for a laryngoscope that can reliably, expeditiously, and consistently deliver an endotracheal tube to a trachea under continuous visualization with a camera, including for patients who are difficult to intubate and/or under the circumstances when suction and/or ventilation may be needed during intubation.

In one embodiment, the present disclosure provides a laryngoscope comprising a handle and a blade,
wherein the handle has a body with a proximal end and a distal end and having a length between the proximal end and the distal end,
wherein the blade is curved and adopted to the contour of a human larynx and wherein the blade has a distal end, a proximal end, a front surface, a back surface, a left flanking surface and a right flanking surface, and
wherein the handle is attached at its distal end to the proximal end of the blade, and
wherein the laryngoscope comprises an endotracheal tube (ETT) channel having a passageway encircled by a wall in the body of at least a portion of the handle length, wherein the ETT channel has a proximal end opening located at or near the proximal end of the handle and wherein the ETT channel has a distal end opening, and
wherein the laryngoscope further comprises a suction/camera channel formed as a passageway in the body of the laryngoscope, wherein the suction/camera channel has a proximal end opening located at or near the proximal end of the handle and wherein the suction/camera channel has a distal end opening located at or near the distal end of the blade and wherein the suction/camera channel has a diameter compatible for positioning a camera in the suction/camera channel.

The laryngoscope may have the blade which contains a protective flange extending distally from the distal end of the blade front surface and wherein the flange is distal to the distal end opening of the ETT channel.

Preferred embodiments of the laryngoscope include those wherein the ETT channel contains a slit opening the ETT channel onto at least one surface of the laryngoscope. In some preferred embodiments, the slit may open the ETT channel to the left flanking surface or to the right flanking surface of the laryngoscope.

In some embodiments, the ETT channel may open with its distal end proximally to or at the distal end of the handle. Some preferred embodiments include laryngoscopes wherein the ETT channel from the handle continues through at least a portion of the blade length and wherein the ETT channel opens with its distal end proximally to or at the distal end of the blade.

In some preferred embodiments, the laryngoscope may comprise one or more guide grooves formed as a recess in at least a portion of the wall of the ETT channel and/or one or more guide grooves formed as a recess in one or more external (the front (ventral) surface, the back (dorsal) surface, the left flank surface or the right flank surface) surfaces of the handle and/or the blade, and wherein a depth of the guide groove is compatible with placing a bougie in the guide groove.

Any of the laryngoscopes according to this disclosure may further comprise a connector extending from the body of the handle, the connector comprising a lumen enclosed by a wall, the lumen opening into the suction/camera channel, wherein the connector is a port for connecting the suction channel to an oxygen, suction and/or vacuum source. Some preferred embodiments include laryngoscopes, wherein the laryngoscope further comprises a suction control port located on the handle, wherein the suction control port is a lumen in the body of the handle and wherein the lumen is connected to the suction channel, and wherein the air pressure inside the suction lumen is controllable by opening and closing the suction control port. In some preferred embodiments, the suction control port may be located in a proximal portion of a front surface of the handle. In some preferred embodiments, the suction control port may be positioned on the front surface of the handle and proximally to the connector positioned on the left flanking surface or the right flanking surface.

Some preferred embodiments of laryngoscopes according to this disclosure include laryngoscopes, wherein the laryngoscope further comprises a cuff attached to the distal portion of the blade, wherein the cuff is located proximally to the distal end of the blade, and wherein the distal end opening for the channel and the distal end opening of the channel located distally to the cuff. The cuff may be inflatable and wherein the laryngoscope further contains a means for inflating the cuff.

In yet another aspect, the present disclosure provides a system comprising the laryngoscope according to this disclosure and wherein the system further comprises one or more of the following items:
 a) a camera adapter, wherein the camera adapter is a substantially cylindrical body enclosing a lumen for housing a camera;
 b) a channel adapter having a substantially conical body formed by a wall that encloses a lumen, the body having a distal end and a proximal end and a length between the distal end and a proximal end, wherein the conical body has a first diameter (d1) at the distal end and a second diameter (d2) at the proximal end, wherein the first diameter (d1) is smaller than the second diameter (d2), and wherein the first diameter (d1) is smaller than a diameter of the proximal end opening of the suction channel, and wherein the second diameter (d2) is larger than the diameter of the proximal end opening of the suction channel;
 c) a bougie; and/or
 d) a camera.

In yet another aspect, the present disclosure relates to an assembly comprising the laryngoscope according to this disclosure, a camera positioned in the suction/camera channel of the laryngoscope and an endotracheal tube positioned in the ETT channel of the laryngoscope.

In one further aspect, the present disclosure relates to method for treating a patient, the method comprising placing a camera into the suction channel of the laryngoscope according to this disclosure and introducing the assembly into patient's upper oral airway. The method may further include manipulating the laryngoscope with assistance by a bougie positioned in a guide groove.

The present disclosure further provides in one embodiment a laryngoscope containing at least one camera/suction channel and/or at least one camera/tool channel. In some embodiments, the laryngoscope may be combined with at least one camera insertable into and removable from the camera/suction channel, the camera providing continuous visualization during insertion and placement.

In one aspect, the present disclosure provides a laryngoscope comprising a camera/suction channel, a handle and a blade with a proximal end and a distal end, the handle comprising a body with a distal end and a proximal end, the body being attached at the distal end to the proximal end of the blade, wherein the blade has a back surface and a front surface, wherein the laryngoscope contains at least one camera/suction entry port located on the body of the handle, the camera/suction entry port opening into the camera/suction channel located inside the body of the handle, the camera/suction channel opening with a camera/suction port on the back surface of the blade. In some embodiments of the laryngoscope, the handle may be attached to the blade removably. In some preferred embodiments of the laryngoscope, the camera/suction channel may comprise a tube. In some preferred embodiments of the laryngoscope, the camera/suction channel may comprise a tube which insertable into and removable from the body of the handle. In some embodiments of the laryngoscope, the body of the handle may further comprise a suction control port. In some embodiments of the laryngoscope, the blade may be curved. In some embodiments, the laryngoscope may further comprise a camera sheath insertable and removable from the camera/suction channel. In some embodiments, the camera sheath may contain a sealed window at the distal end.

In some embodiments, the laryngoscope may further comprise a camera/tool channel attached to the surface of the body of the handle and/or the camera/tool channel comprises a groove shaped in the surface of the body of the handle, wherein the camera/tool channel has a distal end and a proximal end, and wherein the distal end of the camera/tool channel opens on the back surface of the blade or on the side of the back surface of the blade, and wherein the proximal end of the camera/tool channel is positioned on the body of the handle.

In some embodiments, the camera/tool channel may comprise a groove.

In some embodiments, the laryngoscope may further comprise an adaptor attached to the camera/suction entry port.

In some embodiments, the body of the handle may be substantially hollow.

In some preferred embodiments, the laryngoscope may further comprise a camera attached to a wand, the camera being insertable into and removable from the camera/suction channel. The camera may be disposable or it can be reusable. In order to be reusable, the camera may be hosted inside a disposable sheath.

In another aspect, this disclosure relates to an airway management device comprising the laryngoscope according to this disclosure and one or more of the following: at least one camera insertable and removable from the camera/suction channel, at least one bougie and/or at least one stopper for closing the camera/suction entry port.

In yet another aspect, this disclosure relates to a system for endotracheal intubation, the system comprising the laryngoscope according to this disclosure attached to an air/vacuum/suction source and a camera inserted in the laryngoscope and capable of capturing images distally from the back surface of the blade.

In yet further aspect, this disclosure provides a method for managing patient's airway, the method comprising inserting a camera in the camera/suction channel of the laryngoscope according to this disclosure, inserting a bougie into the camera/tool channel, inserting the blade into the oropharynx by manipulating the handle and with assistance from the bougie under continuous visualization by the camera. Some embodiments of the method may further comprise connecting the laryngoscope to an air/suction/vacuum source and establishing suction through the camera/suction channel and aspirating bodily secretions through the camera/suction port. In some embodiments of the method, suction may be conducted under visualization by the camera. The methods may further comprise opening and/or closing the suction control port.

DETAILED DESCRIPTION

This disclosure relates to medical devices for examining and managing a patient airway, including examination, drug-delivery, intubation, ventilation and extubation. In one aspect, this disclosure relates to various embodiments of a laryngoscope, preferably containing an endotracheal tube (ETT) channel suitable for delivering and positioning an endotracheal tube (ETT) during intubation. Some preferred embodiments include means for ventilating a patient through the laryngoscope. In some preferred embodiments, the laryngoscope further preferably comprises a suction channel which may also be used, in at least some embodiments, for housing a camera.

Laryngoscopes according to the present disclosure address certain previously unsolved technical problems, including these laryngoscopes provide a conduit for accurate and expeditious placement of an endotracheal tube wherein the insertion procedure can be performed under continuous visualization and a placement of the laryngoscope and/or the endotracheal tube can be visualized and verified with a camera. Other technical advantages include, but are not limited to, a means for controlling suction, performing suction and placement under continuous visualization, carrying out placement and examination wherein surrounding tissues can be manipulated with a guiding tool, such as for example, as a bougie. Because the laryngoscopes in this disclosure may be assembled with one or more tools, including, but are not limited to, a suction catheter, a camera, a guiding tool, and/or an endotracheal tube, one healthcare practitioner can perform various manipulations as the assembly can be held with one hand while the tools/devices in the assembly can be manipulated and controlled with another hand. The laryngoscopes according to this disclosure can be suitable for use under emergency circumstances and/or for patients who are difficult to intubate. Further embodiments include a laryngoscope containing at least one suction/camera channel and/or at least one camera/tool channel. The laryngoscope is compatible with a camera.

In this disclosure, the term "distal end" means the end which is introduced into a patient's oropharynx first during examination and/or in an intubation procedure. The "proximal end" is opposite to the distal end.

Figure 1:
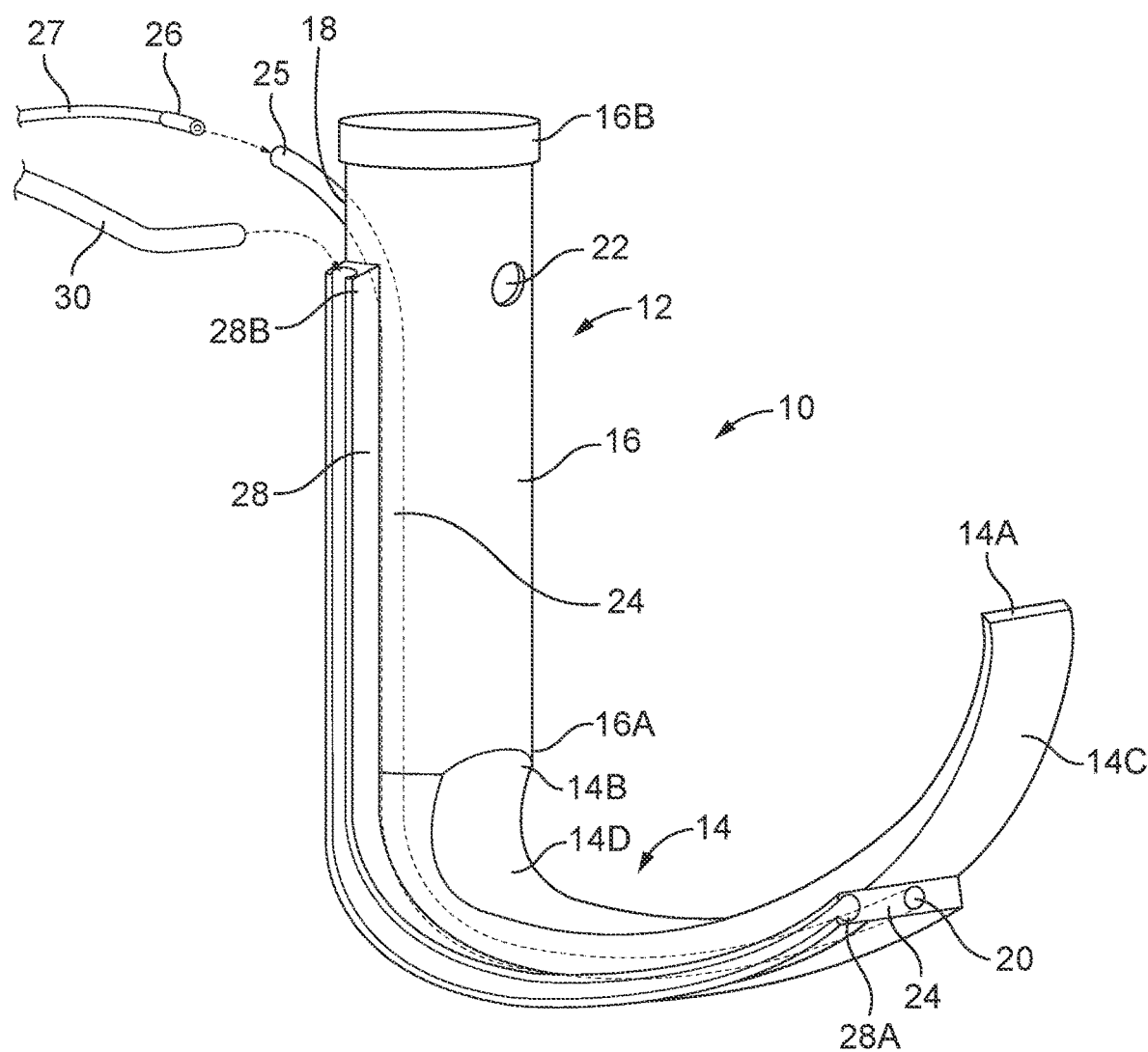
FIG. 1 is a perspective view of one embodiment of a laryngoscope according to this disclosure.

Referring to FIGS. 1-9, certain embodiments of a laryngoscope according to this disclosure will now be described in more detail. FIG. 1 depicts one embodiment of the laryngoscope, generally 10. The laryngoscope 10 comprises a handle 12 and a blade 14. In some embodiments, the handle 12 and the blade 14 are formed into a one-piece laryngoscope during manufacturing. For example, the handle 12 and the blade 14 can be molded together, and/or glued together, or otherwise be permanently attached during manufacturing.

In other embodiments, the handle 12 can be detachable from the blade 14. In these embodiments, the handle 12 can be attached to the blade 14 prior to use, for example, by screwing the handle 12 onto the blade 14 and/or with any other fastener means.

The handle 12 comprises a body 16 with a distal end 16A and a proximal end 16B. It should be noted that while in one embodiment, the handle 12 comprises a substantially tubal body, any other shapes typically used in handles can be also suitable. The shape and the length of the handle 12 can be adjusted as needed.

The blade 14 may be curved and is preferably adopted to the contour of a human larynx such that when the laryngoscope 10 is in use, the blade 14 can be used to lift the epiglottis and can be inserted into an airway by manipulating the handle 12 which remains extended out of the mouth.

The blade 14 has a distal end 14A and a proximal end 14B. The body 16 of the handle 12 is attached at its distal end 16A to the proximal end 14B of the blade 14. In some embodiments, where the handle 12 is detachable from the blade 14, the body 16 may contain a plurality of threads at or near the distal end 16A for screwing the body 16 onto the proximal end 14B of the blade 14. In some embodiments, the blade 14 may comprise a plurality of threads at and/or near the proximal end 14B for attachment to the handle 12.

The blade 14 has a back surface 14C and the opposite front surface 14D. A healthcare professional may grasp the handle 12 and insert the blade 14 into the oropharynx of a patient by manipulating the handle 12 in order to obtain a view of the vocal cords and the glottis and while attempting to gain access to the patient's airway. After the positioning procedure is successfully completed, the front surface 14D of the blade 14 is positioned toward the patient's front, while the back surface 14C is positioned toward the patient's back.

The body 16 contains a suction/camera entry port 18 which is an opening on the body 16. The suction/camera entry port 18 leads to at least one suction/suction channel 24 located inside the body 16 along the proximal-distal axis 16B/16A at least for a portion of the length of the body 16. The suction/camera channel 24 opens on the back surface 14C of the blade 14 with at least one camera/suction port 20.

In some embodiments, the suction/camera channel 24 comprises a passage inside the handle 12 located along the proximal-distal axis 16B/16A for at least a portion of the body 16 length. In some embodiments, the suction/camera channel 24 may be continued further from the body 16 and inside the blade 14 and then open on the back surface 14C of the blade 14 with at least one camera/suction port 20. In at least some embodiments, the suction/camera channel 24, for example as a tubing, may start at or near the camera/suction entry port 18, located inside the body 16 and then be continued outside the blade 14 and in some embodiments, be continued outside and along at least a portion of the back surface 14C of the blade 14.

In some embodiments, the body 16 is hollow at least partially. This is one of the technical advantages of the laryngoscope according to this disclosure versus video laryngoscopes known in the art. While handles in conventional laryngoscopes often host batteries, one or more power switches and other elements, making a conventional handle heavy and difficult to manipulate, the handle 12 in some preferred embodiments need not to include any such elements. In some preferred embodiments, the body 16 is substantially hollow (having a space inside), providing a space for the suction/camera channel 24. In some other embodiments, the body 16 is not hollow and instead it can be made as a solid piece in which the suction/camera channel 24 may be bored through.

In some embodiments, the suction/camera channel 24 may comprise a tubing, a portion of which may protrude outside the camera/suction entry port 18. This portion of the tubing protruding outside the camera/suction entry port 18 may be used as an adaptor 25. The adaptor 25 can be used for connecting the laryngoscope 10 to an oxygen/suction/vacuum source (not shown). The adaptor 25 may further comprise a valve, e.g., a clip, which may regulate opening and closing of the camera/suction entry port 18.

In some embodiments, the tubing which comprises the suction/camera channel 24 can slide proximally/distally. In some embodiments, the tubing can be insertable and removable from the laryngoscope 10.

A camera 26 connected to a wire, a cable and/or a wand 27 can be placed through the camera/suction entry port 18 into the suction/camera channel 24 and then positioned at the camera/suction port 20. In some embodiments, the camera 26 with the wand 27 can further comprise a sheath. In some embodiments, the sheath may comprise a sealed window at its distal end. The camera 26 with the wand 27 may be placed and in the sheath and removed from the sheath, as needed. The sheath protects the camera from exposure to bodily fluids. In embodiments, wherein the suction/camera channel 24 comprises a tubing, the tubing may serve as the sheath for the camera 26 and the wand 27 and/or the tubing.

Figure 2:
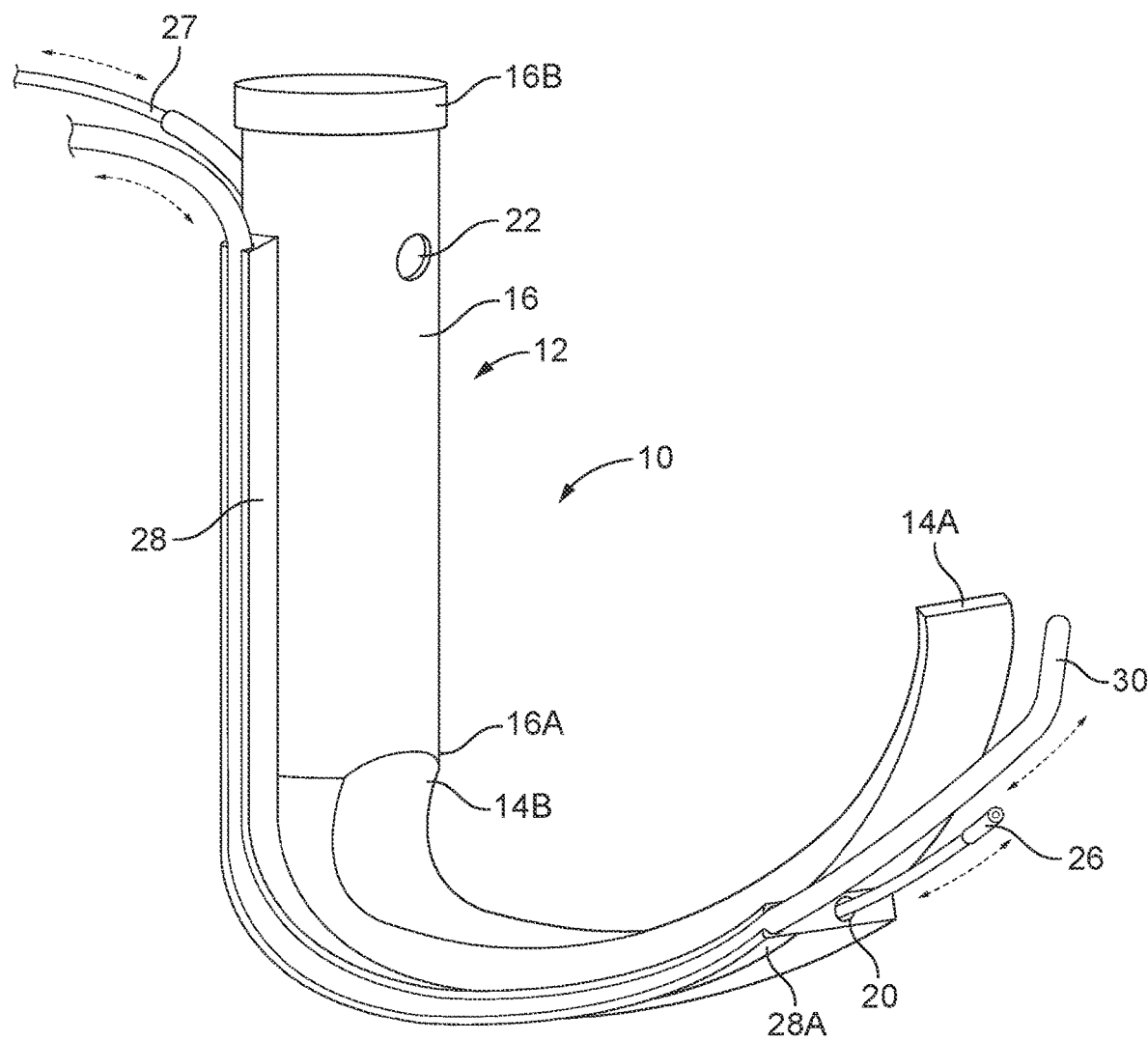
FIG. 2 is a perspective view of an embodiment of a laryngoscope according to this disclosure, including a camera inserted into the suction/camera channel and a bougie inserted into the camera/tool channel.

In some embodiments and as is shown in FIG. 2, the camera 26 with the wand 27 can slide inside the suction/camera channel 24. The camera 26 can extend distally from the camera/suction port 20. This provides visualization of a patient's larynx and vocal cords in real time. The positioning of the camera 26 relative to the camera/suction port 20 can be adjusted as needed by manipulating the wand 27.

Figure 5:
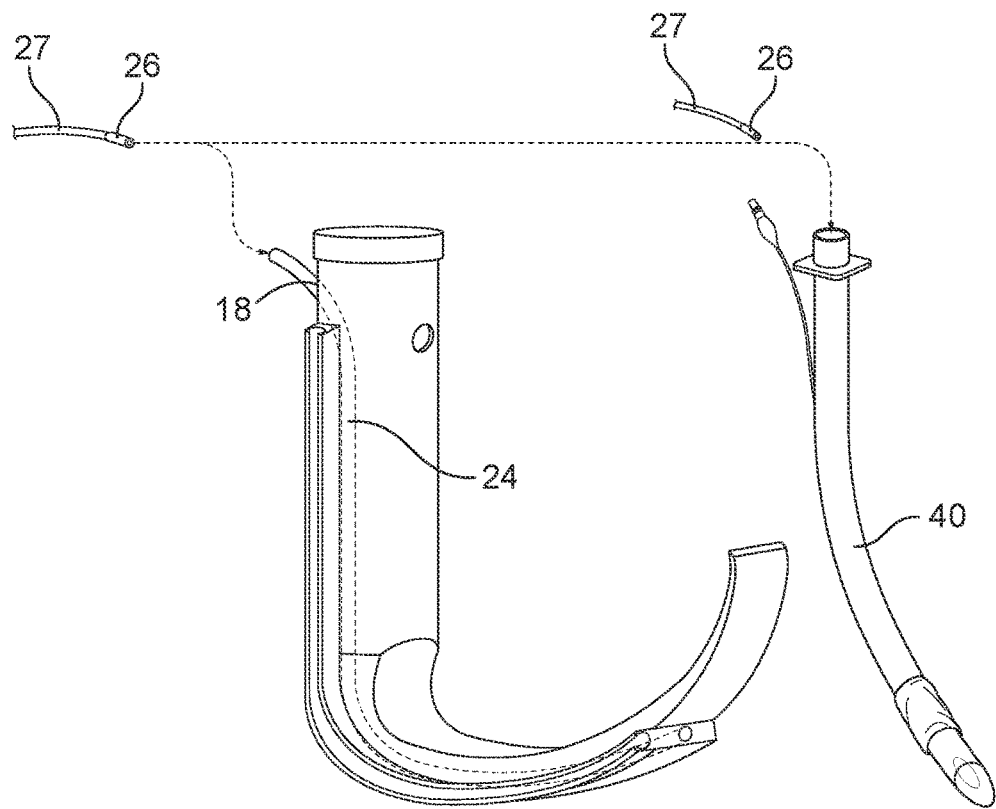
FIG. 5 is a perspective view of an embodiment of the laryngoscope of FIG. 1 with a camera and an endotracheal tube.

As shown in FIG. 5, the camera 26 with the wand 27 can be removed from the suction/camera channel 24 through the camera/suction entry port 18 while the laryngoscope 10 remains positioned in a patient. This feature provides yet another technical advantage.

The camera 26 can be then used in combination with another medical device, for example, with an endotracheal tube 40, as shown in FIG. 5.

In some embodiments and as is shown in FIGS. 1 and 2, the laryngoscope 10 may further comprise at least one camera/tool channel 28 with a distal end 28A and a proximal end 28B. The camera/tool channel 28 is positioned outside the body 16.

While the camera/tool channel 28 may be positioned anywhere on the surface of the body 16, some preferred embodiments include those wherein the positioning of the camera/tool channel 28 relative to the back surface 14C is such that the camera/tool channel 28 is adjacent to the surface 14C. Preferably, the camera/tool channel 28 is positioned on the side of the back surface 14C.

Preferably, the distal end 28A of the camera/tool channel 28 is located on the back surface 14C of the blade 14 or the distal end 28A of the camera/tool channel 28 is located on the side of the back surface 14C. Preferably, the proximal end 28B is located on the surface of the body 16.

In some embodiments, the camera/tool channel 28 may comprise a tube, a tube with a split, a groove, a set of clip-like holders or any combination therefor attached to the external surface of the body 16. In other embodiments, the camera/tool channel 28 may be a groove or a channel shaped in the wall of the body 16.

Figure 3:
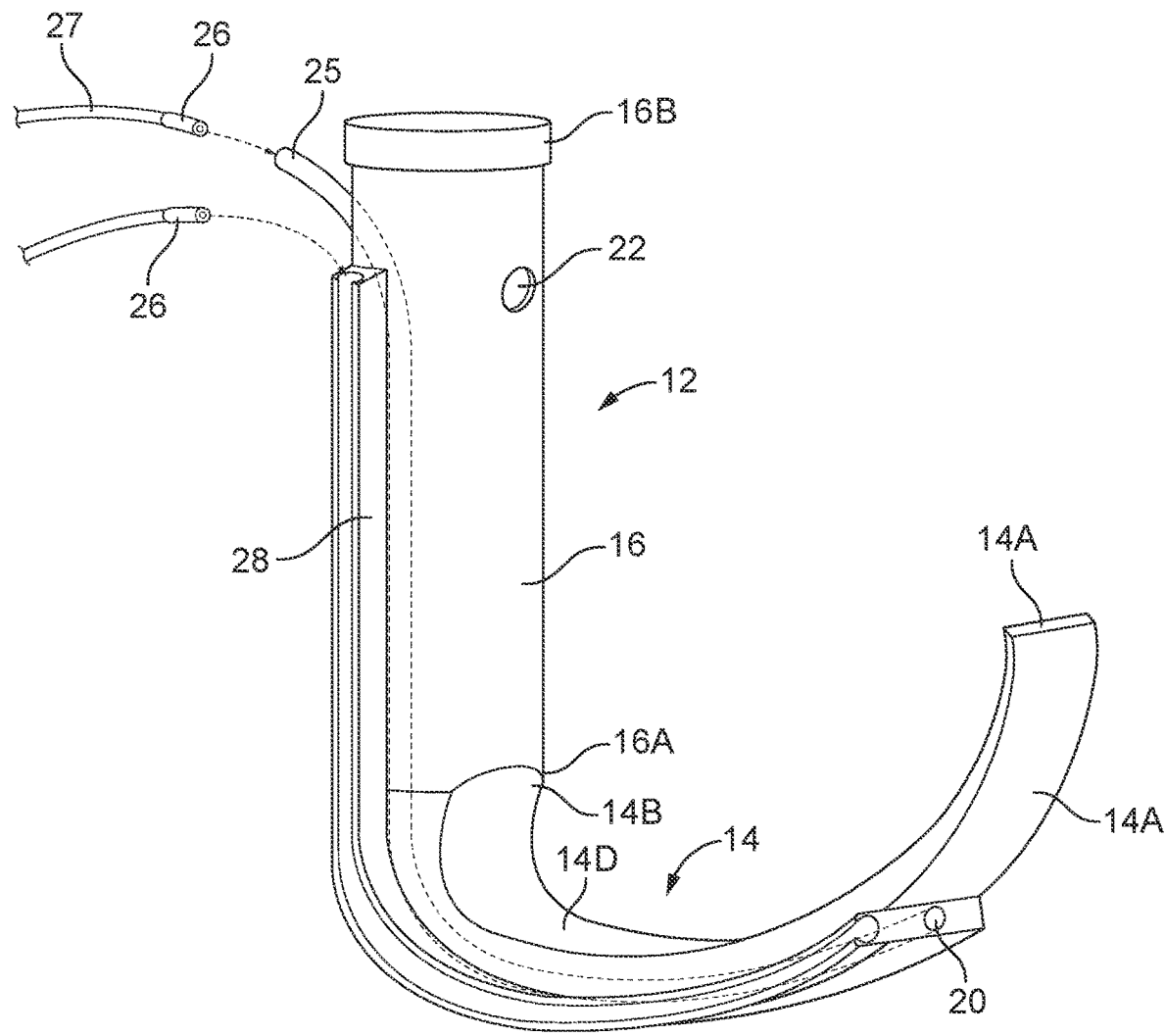
FIG. 3 is a perspective view of an embodiment of a laryngoscope according to this disclosure and which can be combined with two cameras.
Figure 4:
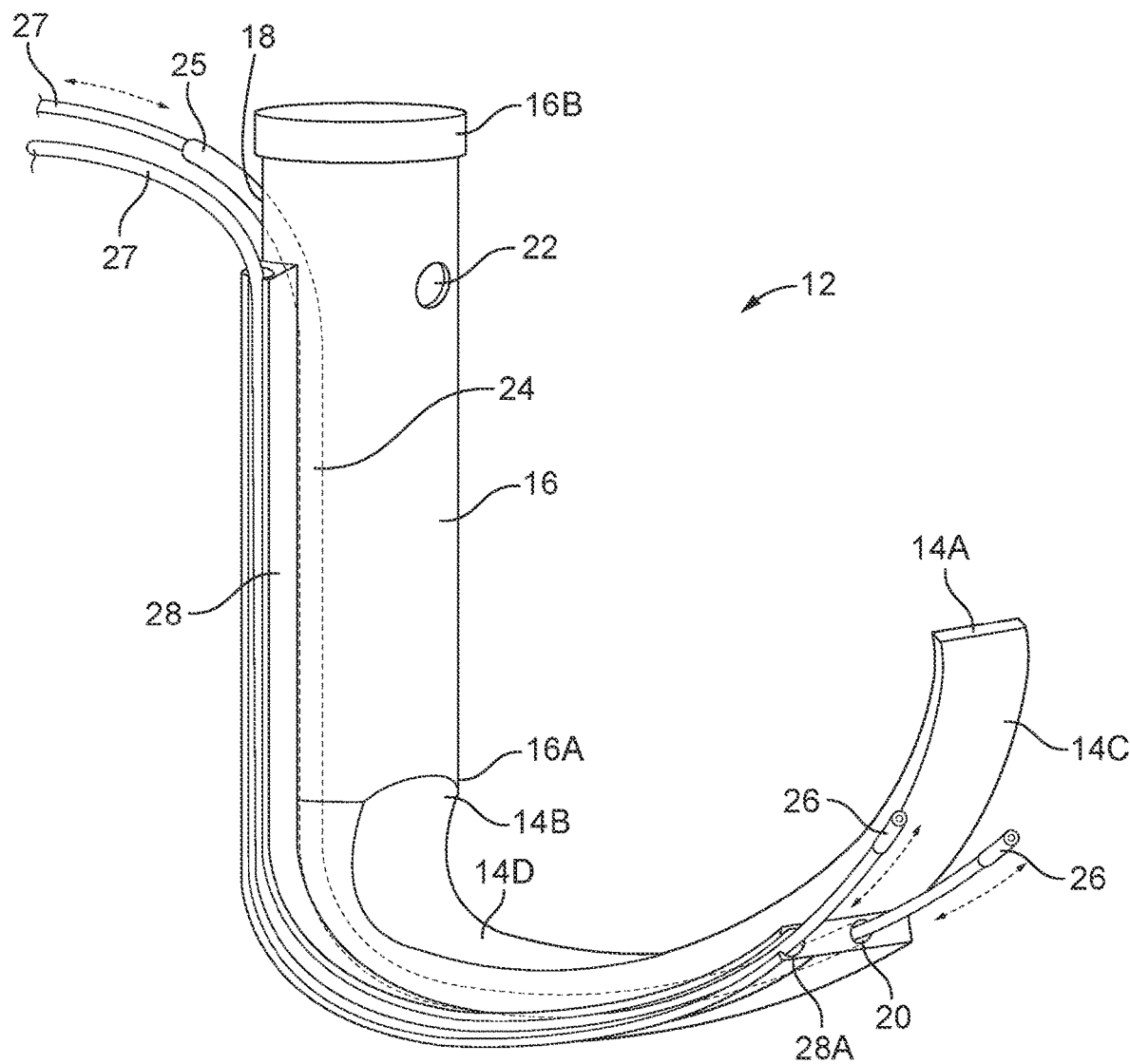
FIG. 4 is a perspective view of the laryngoscope of FIG. 3 with a first camera extending distally from the suction/camera channel and a second camera extending distally from the camera/tool channel.

The camera/tool channel 28 can host a tool or a camera. For example, the camera/tool channel 28 can host a bougie 30, as shown in FIG. 2 or a second camera 26 as shown in FIGS. 3 and 4 or a suction tube (not shown).

As shown in FIG. 2, because the distal end 28A of the camera/tool channel 28 opens on the back surface 14C or on the side of the back surface 14C of the blade 14, the bougie 30 can extend distally from the camera/tool channel 28 and it can slide proximally/distally. The tip of the bougie 30 can be positioned distally relative to the camera 26 which is extending distally from the camera/suction port 20, as shown in FIG. 2.

As shown in FIG. 2, a healthcare professional can adjust a relative position of the bougie 30 in the channel 28 and the camera 26 in the channel 24 such that the bougie 30 is manipulated in an oral airway under continuous visualization by the camera 26. Because the bougie 30 is hosted in the camera/tool channel 28, the bougie 30 can be removed, while the laryngoscope 10 remains positioned in a patient. Furthermore, because the camera 26 and the bougie 30 are held in place by the respective channels 24 and 28, one healthcare professional can manipulate and adjust the camera 26, the laryngoscope 10, and the bougie 30.

Figures 6, 7:
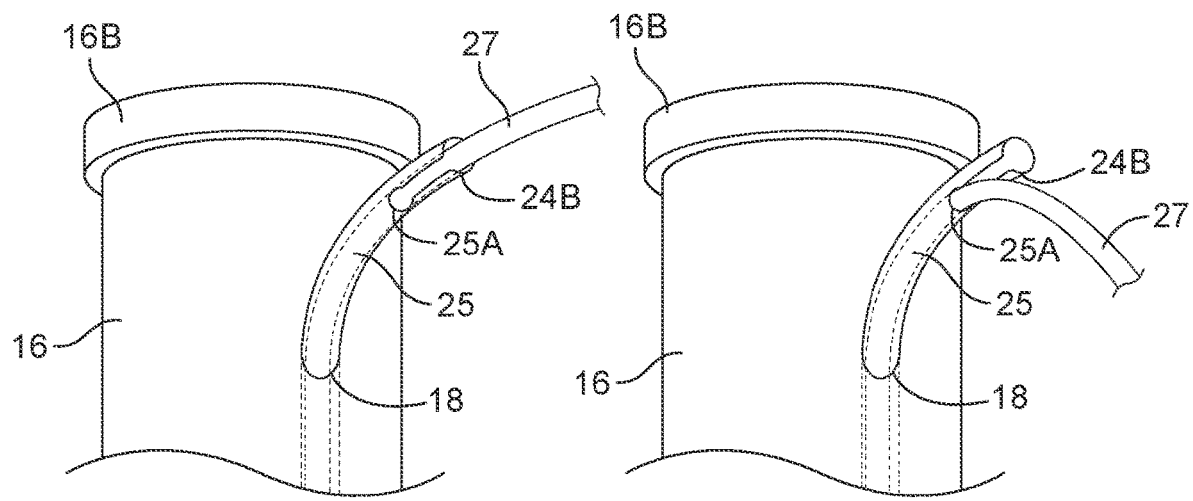
FIG. 6 depicts a portion of one embodiment for a laryngoscope handle with an adaptor and a camera being inserted into the suction/camera channel.
FIG. 7 depicts a portion of one embodiment for a laryngoscope handle with a camera being inserted into the suction/camera channel and camera's wand being secured in place.

As is shown in FIGS. 6 and 7, the adaptor 25 may comprise a tube which may have a notch 25A near the proximal end. The notch 25A can be used for securing the wand 27 after the camera 26 has been inserted into the suction/camera channel 24. The notch 25A holds the wand 27 in place and prevents it and the camera 26 from sliding distally and deeper into the laryngoscope 10. Once the position of the camera 26 is adjusted and verified as being located distally from the camera/suction port 20, the wand 27 can be secured in the notch 25A. This provides yet another technical advantage as the laryngoscope 10 and the bougie 30 can be manipulated by one healthcare professional under continuous visualization from the camera 26.

Figure 9:
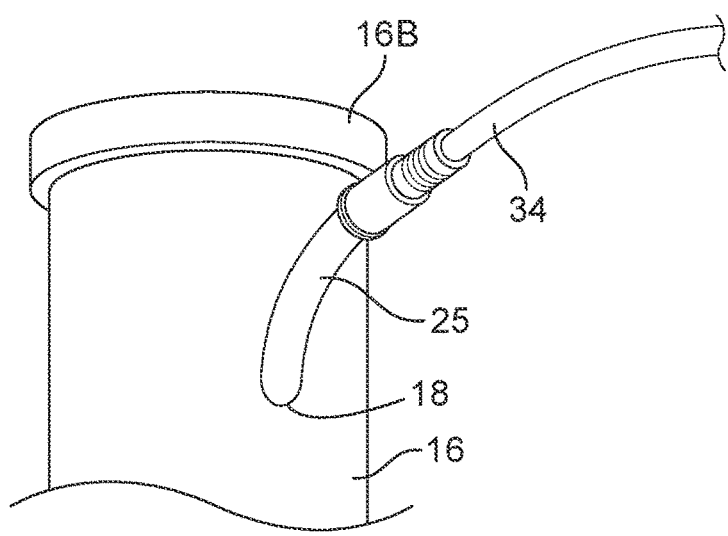
FIG. 9 depicts a proximal portion of the laryngoscope handle of FIG. 8, showing the adaptor being connected to a succession catheter.

Yet another technical advantage of the laryngoscope according to this disclosure is that the camera/suction entry port 18 may be also used as a suction port. When suction is needed, for example, because an airway is obstructed with vomit, blood, and/or some other bodily secretion, a healthcare professional may remove the camera 26 from the suction/camera channel 24 and connect the adaptor 25 to a suction catheter 34, one embodiment of which is shown in FIG. 9. In at least some other embodiments, the camera 26 need not be removed before suction can take place. In these embodiments, the camera 26 can remain placed in the channel 24 during suction through the channel 24.

The suction catheter 34 may be connected to a suction/vacuum source (not shown). A bodily secretion is then aspirated into the camera/suction port 20 and suctioned out through the suction/camera channel 24 and removed from the camera/suction entry port 18.

In some embodiments, the body 16 may comprise a suction control port 22 which opens inside the body 16. The suction control port 22 is connected to the suction/camera channel 24. When the suction control port 22 is open, it supplies air to the suction/camera channel 24. Accordingly, vacuum in the suction/camera channel 24 is released at least partially through the suction control port 22 and suction through the suction/camera channel 24 is decreased at least partially. Thus, the suction control port 22 controls suction or it can be used to decrease suction through the suction/camera channel 24.

Figure 8:
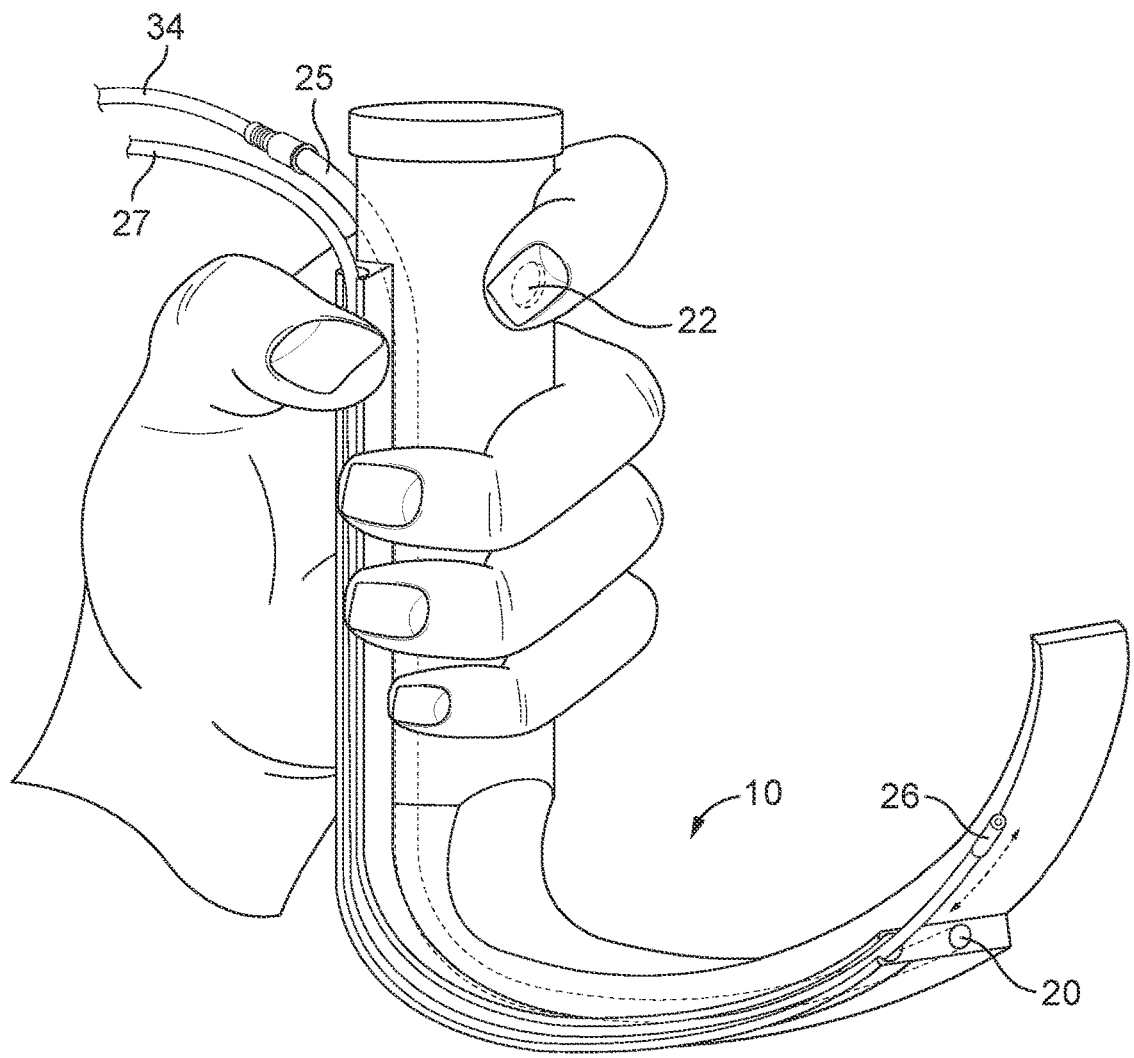
FIG. 8 depicts one embodiment of the laryngoscope of this disclosure in use and connected through a suction catheter to a suction/vacuum source (not shown).

As shown in FIG. 8, a healthcare professional may close the suction control port 22 with a finger, a piece of tape and/or a suction control port may be fitted with a stopper/plug/lid (not shown). If no suction is needed or only minimum suction is needed, the suction control port 22 may be kept open. In order to increase suction and aspiration of bodily secretions from the camera/suction port 20, the suction control port 22 may be closed with a finger or with a stopper/plug/lid (not shown in FIG. 8).

As shown in FIG. 8, a camera 26 can be positioned in the camera/tool channel 28 and/or the camera 26 may remain positioned in the suction/camera channel 24 and accordingly, suction through the camera/suction port 20 can be conducted under continuous visualization from the camera 26 positioned in the camera/tool channel 28. Because suction is conducted under visualization with the camera 26, a healthcare professional can monitor the process in real time and by applying only minimum vacuum as may be needed in order to prevent damage to the surrounding tissues.

The laryngoscopes of this disclosure provide several technical advantages, some of which are described in more detail below. If needed, a placement of the laryngoscope 10 can be assisted by a bougie 30 under continuous visualization with one or more cameras 26. If needed, the camera 26 and/or the bougie 30 can be removed, while the laryngoscope 10 remains positioned in a patient. By monitoring the surrounding tissues in real time with one or more cameras 26, a healthcare professional can complete laryngoscopy and/or endotracheal intubation in a shorter period of time. A correct placement can be verified in real time. If/when suction may be needed, a healthcare professional can initiate suction while still holding the laryngoscope 10. One healthcare professional can operate the laryngoscope 10, the suction catheter 34 and the camera 26 with one hand by simply holding the laryngoscope handle 12.

Because the laryngoscope 10 and suction can be operated under continuous visualization, this may decrease a risk of trauma to patient's surrounding tissues and help with intubation of a difficult airway. The intubation can be completed faster and with fewer attempts. In some embodiments, the laryngoscope 10 may be made light in weight and portable as it does not need to include a battery and/or a power switch in the handle, lessening a burden on a healthcare professional handling the laryngoscope 10 during a procedure.

In another aspect, the present disclosure provides a system comprising the laryngoscope 10 and one or more of the following: at least one camera with a cable and/or wand, the camera insertable into and removable from the channel 24 and/or the channel 28, and/or at least one bougie insertable into and removable from the channel 28, and/or a stopper that can fit into the suction control port 22; and/or suction tubing insertable into and removable from the port 18 and the port 20; and/or an instruction manual.

Referring to FIGS. 10-32, further embodiments of a laryngoscope according to this disclosure will now be described in more detail.

FIGS. 10, 11, 14, 15, 16, 23, 24 and 27 depict various views of an alternative embodiment of the laryngoscope according to this disclosure, generally 100. The laryngoscope 100 comprises a handle 112 attached to a blade 114. In some embodiments, the handle 112 and the blade 114 are formed into a one-piece laryngoscope during manufacturing, for example by molding. In some embodiments, the handle 112 and the blade 114 can be molded together, and/or glued together, or otherwise be permanently attached during manufacturing. In other embodiments, the handle 112 can be detachable (not shown) from the blade 114. In these embodiments, the handle 112 can be attached to the blade 114 prior to use, for example, by screwing the handle 112 onto the blade 114 and/or with any other fastener means.

Preferably, the handle 112 has a substantially tubal body having a length between a proximal end 112P and a distal end 112D. It should be noted that while in one embodiment, the handle 112 has a substantially tubal body, any other shapes typically used for handles can be also suitable. The shape and the length of the handle 112 can be adjusted as needed in order to facilitate a sufficient grasp by a healthcare professional for manipulating the handle 112 during insertion and while conducting examination and/or intubation.

The handle 112 has a front surface 112F and the opposite back surface 112B. In this disclosure, the front surface can be alternatively referred to as "the ventral surface." In this disclosure, the back surface can be alternatively referred to as "the dorsal surface."

The handle 112 also has two flanking surfaces, the right flanking surface 112R and the left flanking surface 112L. As can be seen in the cross-sectional view of FIG. 16, the flanking surface 112L is located between the front surface 112F and the back surface 112B, creating one flank and the flanking surface 112R is located between the back surface 112B and the front surface 112F, creating the other flank.

Figure 10:
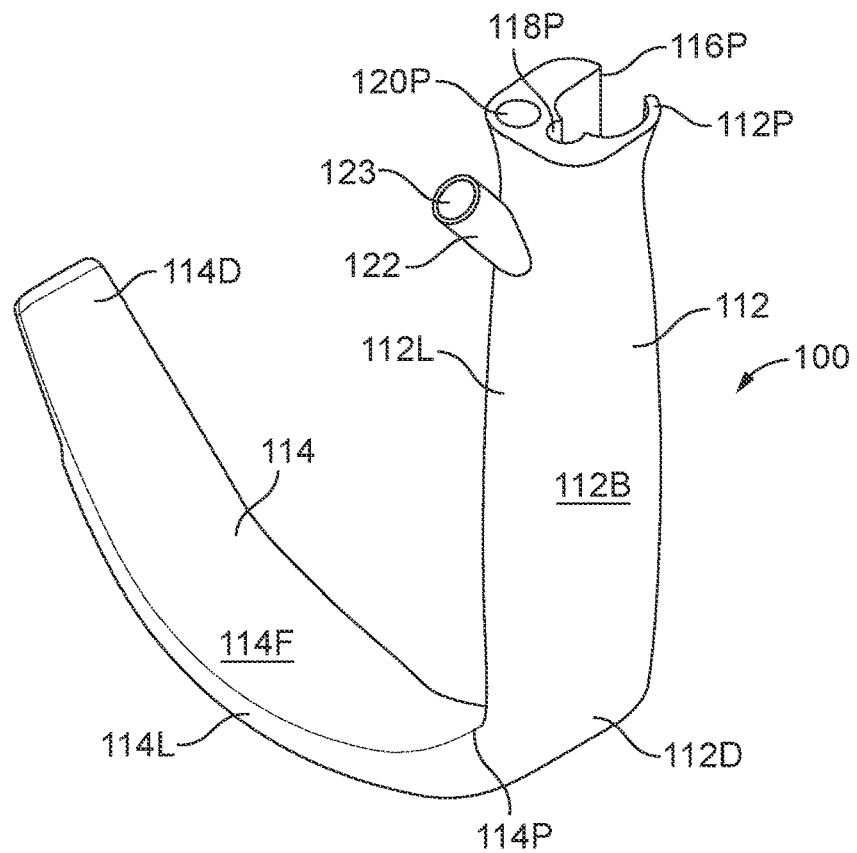
FIG. 10 depicts a perspective view of one embodiment of a laryngoscope according to this disclosure showing a front (ventral) surface of the blade.

In some embodiments, a width of the handle 112 which can be defined as the width of the front surface 112F from the left flank 112L to the right flank 112R is substantially same as a width of the blade 114 which can be measured as the width of the blade front surface 114F from the left flank 114L to the right flank 114R one embodiment of which is shown in FIG. 10. In other embodiments, the width of the handle 112 is less than the width of the blade 114 and the blade 114 is wider (broader)a than the handle 112.

The blade 114 may be curved and is preferably adopted to fit with the contour of a human larynx such that when the laryngoscope 100 is in use, the blade 114 is insertable into the human larynx and the blade 114 can be used to lift the epiglottis. The blade 114 can be introduced into an oropharynx by manipulating the handle 112 which may remain substantially extended out of the mouth in some embodiments. In some preferred embodiments, the blade 114 is shaped such that it can extend to the hypopharynx and glottic structures. The blade 114 may be sufficiently rounded to pass over the patient's tongue.

The blade 114 has a distal end 114D and a proximal end 114P. The handle 112 is attached at its distal end 112D to the proximal end 114P of the blade 114. In at least some embodiments, the blade 114 is attached to the handle 112 at an angle α such that the laryngoscope 100 is J-shaped. The angle α can be optimized as needed, and preferably it can be at any value between 30 and 150 degrees. Other values can be also suitable. The angle α is optimized based on the angle needed for performing functions such as passing over the tongue and lifting the epiglottis with as little manipulation of the head and the neck as possible. In some embodiments, the blade 114 is wider (broader) than the handle 112.

The blade 114 has a back (dorsal) surface 114B and the opposite front (ventral) surface 114F. A healthcare professional may grasp the handle 112 and introduce the blade 114 into the oropharynx of a patient by manipulating the handle 112 in order to obtain a view of the vocal cords and the glottis and while attempting to gain access to the patient's airway.

The blade 114 has two flanking surfaces, the right flanking surface 114R and the left flanking surface 114L. As can be seen for example in FIG. 11, the flanking surface 114L is located between the front surface 114F and the back surface 114B, creating one flank. The opposite flank (not shown in FIG. 11, but the opposite flank can be seen in FIG. 24) has a flanking surface 114R is located between the back surface 114B and the front surface 114F on the opposite site of the left flanking surface 114R.

At its proximal end 114P, the front surface 1114F of the blade 114 is connected to the distal end 112D of the front surface 112F of the handle 112. The front surface 114F of the blade 114 and the front surface 112F of the handle 112 can be collectively referred to in this disclosure as the front surface of the laryngoscope 110.

At its proximal end 114P, the back surface 114B of the blade 114 is connected to the distal end 112D of the back surface 112B of the handle 112. The back surface 114B of the blade 114 and the back surface 1112B of the handle 112 can be collectively referred to in this disclosure as the back surface of the laryngoscope 100.

At its proximal end 114P, the left flanking surface 114L of the blade 114 is connected to the distal end 112D of the left flanking surface 112L of the handle 112. The left flanking surface 114L of the blade 114 and the left flanking surface 112L of the handle 112 can be collectively referred to in this disclosure as the left flanking surface of the laryngoscope 100.

At its proximal end 114P, the right flanking surface 114R of the blade 114 is connected to the distal end 112D of the right flanking surface 112R of the handle 112. The right flanking surface 114R of the blade 114 and the right flanking surface 112R of the handle 112 can be collectively referred to as the right flanking surface of the laryngoscope 100.

When a healthcare professional holds the laryngoscope 100 by the handle 112 and is looking at the blade front surface 114F with the distal end 114D pointing away from the healthcare professional, the blade right flanking surface 114R is on the right from the healthcare professional.

In some embodiments, the blade 114 may contain a protective flange 115 extending distally from the distal end 114D of the front surface 114F. In some preferred embodiments, the protective flange 115 is the first area of the laryngoscope 100 that contacts the epiglottis during insertion. Accordingly, the protective flange 115 may be made in a shape and of a material facilitating insertion, e.g., aiding in lifting the epiglottis, while also protecting patient's tissues from injuries. Some preferred shapes for the protective flange 115 include, but are not limited to, a tongue-like shape tapered at its distal end. Suitable materials for making the flange 115 include plastic.

As can be seen for example in FIG. 16, which is a cross-sectional view, the handle 112 in some preferred embodiments can be made as a solid-piece body 113, e.g., a plastic body, in which various channels, lumens and recesses, e.g., 116, 118 and 120 are located, as discussed in more detail below. The blade 114 can be also made as a solid-piece body 117, e.g., a plastic body, in which various channels are located. In this disclosure, the body 113 of the handle 112 together with the body 117 of the blade 114, can be referred as the body of the laryngoscope 100.

Some laryngoscopes according to this disclosure comprise a channel 116 suitable for carrying an endotracheal tube (ETT). The ETT channel 116 can be referred in this disclosure interchangeably as the ETT conduit or as the ETT channel because one of the functions for the ETT channel 116 is to guide an ETT during an intubation procedure. Insertion of an ETT can be guided and adjusted by manipulating the handle 112 of the laryngoscope 100 with one hand.

Figure 16:
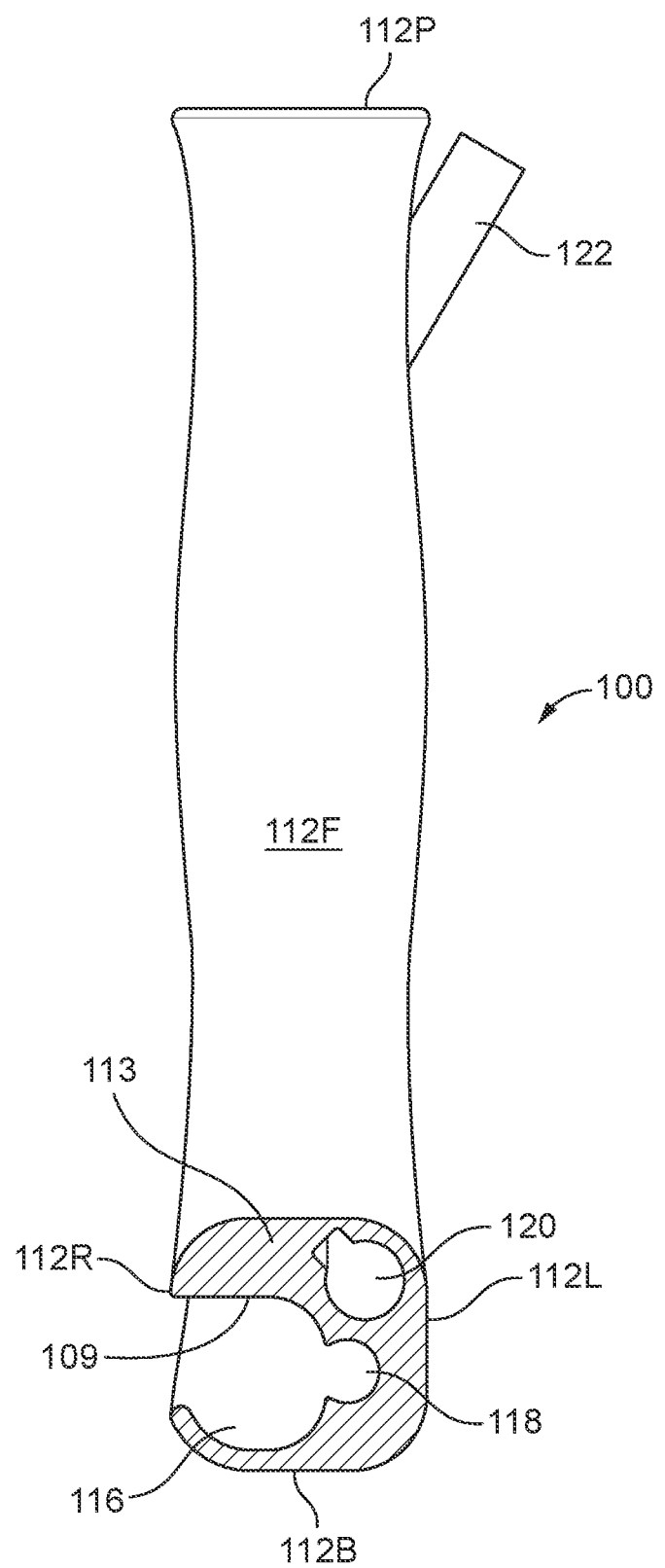
FIG. 16 is a cross-sectional view of the laryngoscope according to this disclosure taken through the handle from the front surface to the back surface and perpendicular to the proximal-distal 12P/12D axis.

Unlike prior art laryngoscopes, where an endotracheal tube is typically positioned externally on the surface of a handle, the ETT channel 116 in preferred embodiments of the laryngoscopes according to this disclosure is a passageway (a lumen, channel or a groove) in the body of at least a portion of the handle length 112, one embodiment of which can be seen in a cross-sectional view in FIG. 16.

In some embodiments, the ETT channel 116 starts with an opening 116P at or near the proximal end 112P of the handle 112. The opening 116P leads into a passageway (lumen) in the body 113 of the handle 112. In some embodiments, the ETT channel 116 can be extruded in the body of the laryngoscope 100. In some embodiments, the laryngoscope 100 can be molded with the lumen for the ETT channel 116. In some embodiments, the lumen of the ETT channel 116 is at least partially encircled by the wall of 109.

Preferably, the ETT channel 116 continues through at least a portion or even all the length of the handle 112 along the proximal-distal axis 112P/112D. The ETT channel 116 may further preferably continue as a passageway in the body 117 through at least a portion of the length of the blade 114 along the proximal-distal axis 114P/114D, as shown for example in FIG. 11. In other embodiments, the ETT channel 116 is located in the handle 112.

In some preferred embodiments, the ETT channel 116 ends with an opening 116D at or near the distal end 114D of the blade 114. A diameter of the ETT channel 116 may vary, but typically it is compatible with a diameter of an endotracheal tube such that an endotracheal tube, e.g., an endotracheal tube 406, can be placed into the ETT channel 116 for example, as shown in FIG. 23, depicting the endotracheal tube 406 positioned in the ETT channel 116.

Figure 23:
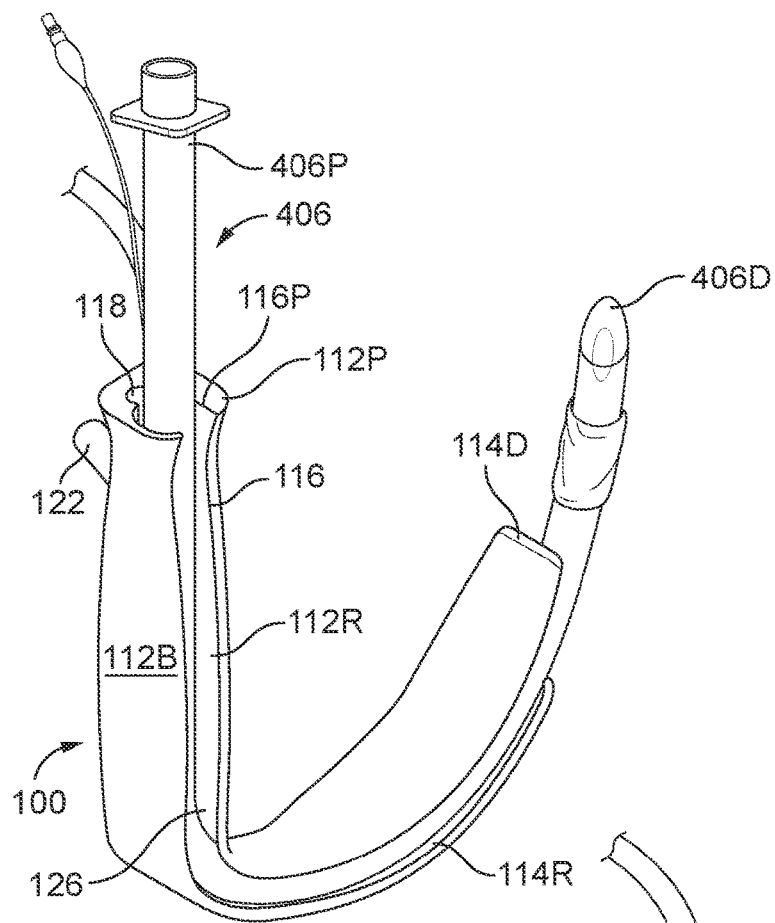
FIG. 23 depicts a side perspective view of one embodiment of the laryngoscope according to this disclosure with an endotracheal tube positioned in the ETT channel and extending distally from the distal end of the laryngoscope.

As shown in FIG. 23, when the endotracheal tube 406 is placed in the ETT channel 116, a distal end 406D of the endotracheal tube 406 may extend distally out from the distal opening 116D of the ETT channel 116. The diameter of the ETT channel 116 is preferably larger than a diameter of an endotracheal tube such that an endotracheal tube can slide inside the ETT channel 116 along the proximal-distal axis 112P/114D of the laryngoscope 100. Endotracheal tubes include those suitable for infants, pediatric patients, adult female patients or adult male patients. Accordingly, the diameter of the ETT channel 116 can be adopted in order to carry an endotracheal tube with an ETT diameter of 3 mm as typically used in infants, of 6.0 to 6.5 mm as typically used in pediatric patients, or form an ETT with a larger diameter, e.g., 7.5 to 8.0 mm or even 8 to 8.5 mm as used for adult patients.

The endotracheal tube 406 may further extend distally from the distal end 114D of the blade 114. A proximal end 406P of the endotracheal tube 406 may extend proximally from the proximal opening 116P of the ETT channel 116. In some embodiments, certain laryngoscopes according to this disclosure may serve as a conduit for delivering and positioning an endotracheal tube during intubation.

Figure 24:
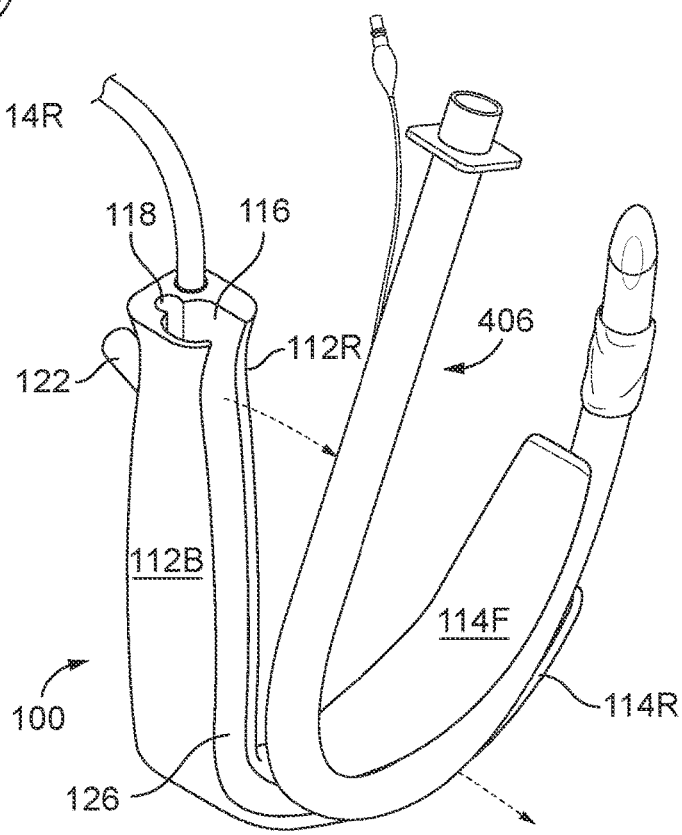
FIG. 24 depicts the endotracheal tube being separated from the laryngoscope through the slit in the ETT channel.
Figures 25, 26:
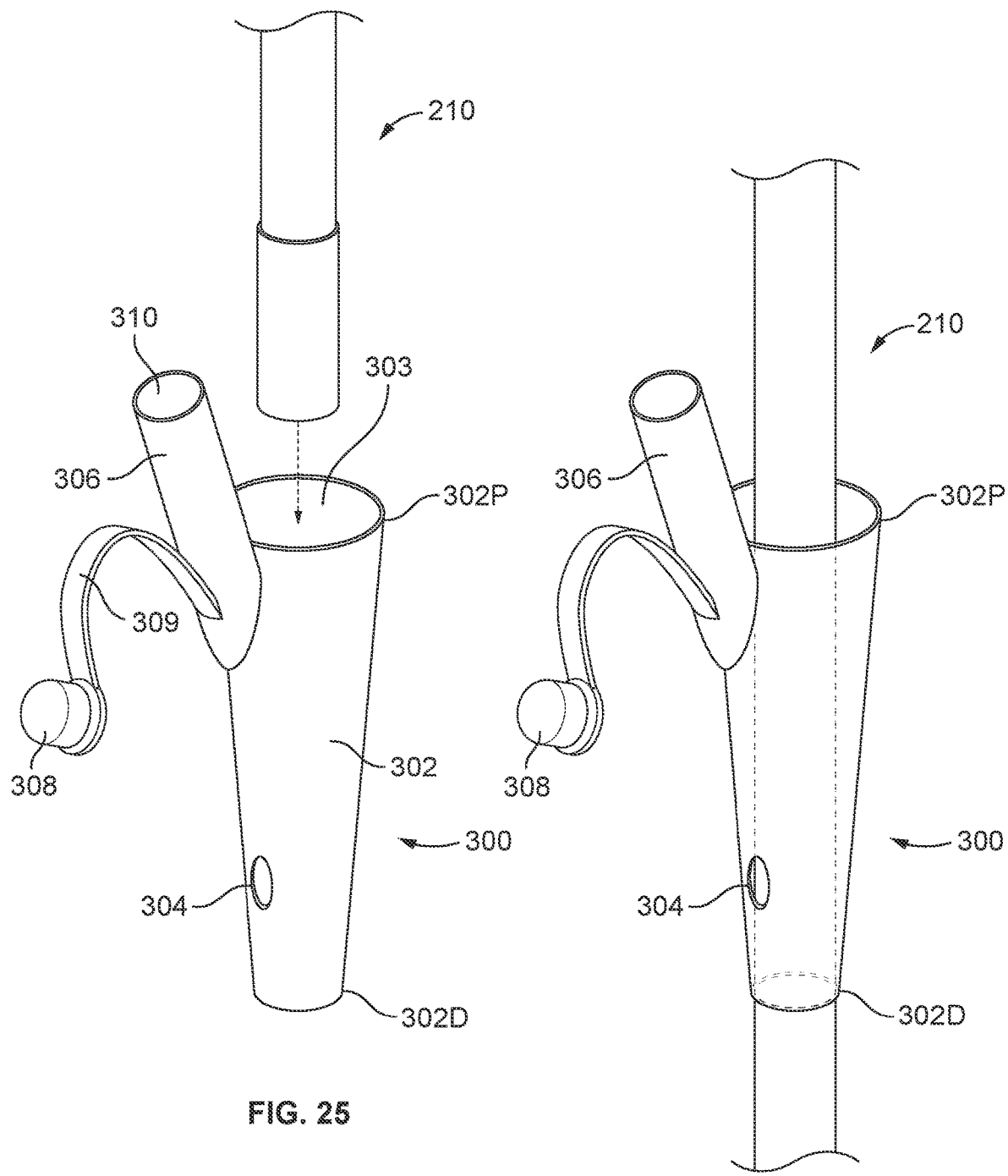
FIG. 25 depicts one embodiment of an adapter.
FIG. 26 depicts the adapter of FIG. 25 being combined with a camera.

In some embodiments, the ETT channel 116 may comprise a slit 126 as shown in FIG. 24. In some embodiments, the slit 126 may be in a form of a groove. The slit 126 may be running for at least a portion of the length of the ETT channel 116. The slit 126 opens the ETT channel 116 onto at least one of the surfaces of the laryngoscope 100. In some preferred embodiments, the slit 126 opens the ETT channel 116 to one or more of the flanking surfaces 112L, 114L, 112R and/or 114R. Preferably, the slit 126 opens to the right flanking surfaces 112R and 114R or to the left flanking surfaces 112L and 114L.

As shown in FIG. 24, in one preferred embodiment, an endotracheal tube 406 can be positioned into the ETT channel 116 and removed from the ETT channel 116 through the slit 126 that opens the ETT channel 116 to the right flanking surfaces 112R and/or 114R. In alternative embodiments, an endotracheal tube 406 can be positioned into the ETT channel 116 and removed from the ETT channel 116 through the slit 126 that opens the ETT channel 116 to the left flanking surfaces 112L and/or 114L. In yet another alternative embodiment, an endotracheal tube 406 can be positioned into the ETT channel 116 and removed from the ETT channel 116 through the slit 126 that opens the ETT channel 116 to the back surfaces 112B and/or 114B. In yet another alternative embodiment, an endotracheal tube 406 can be positioned into the ETT channel 116 and removed from the ETT channel 116 through the proximal end opening 116P.

Some embodiments of the ETT channel 116 do not comprise the slit 126. In some embodiments, the ETT channel 116 may be a lumen substantially enclosed by the wall 109 of the body 113 of the handle 112. In some embodiments, the ETT channel 116 may continue as a lumen substantially enclosed by the wall 109 of the body 117 of the blade 114. In other embodiments, the ETT channel 116 may run only through the handle 112 and open with the distal end opening 116D at or near the distal end 112D of the handle 112, while the blade 114 does not contain the EET channel 116 located inside the body of the blade 114.

It should be further noted that in yet some other embodiments, the ETT channel 116 may be formed, e.g., it may be extruded, as a groove, a trench or a recess in the body 113 of the handle 112 for at least a portion of the handle length along the proximal-distal axis 112P/112D and then preferably continued as a groove, a trench, a recess or a lumen in the body 117 of the blade 114 for at least a portion of its length along the proximal-distal axis 114P/114D. In any of these embodiments, the ETT channel 116 may open onto either the flanking surfaces, 112L and/or 114L, or 112R and/or 114R, or the back surfaces 112B and/or 114B. Embodiments wherein the ETT channel 116 is formed as a groove, a trench, a recess and/or the ETT channel contain the slit 126 facilitate removing an endotracheal tube from the ETT channel 116 after the intubation is completed.

The ETT channel 116 provides several technical advantages, some of which are outlined below. First, the endotracheal tube 406 when positioned in the ETT channel 116 moves together with the laryngoscope 100 and a health care practitioner can perform insertion with one hand by manipulating the handle 112.

Second, as the ETT channel 116 is located inside the handle 112, it is less likely that the endotracheal tube 406 will separate from the laryngoscope 100 during insertion.

In third, because the ETT channel 116 is located inside the handle 112, the ETT channel 116 protects the ETT 406, e.g., from involuntary bites, scratches and/or deformation during insertion.

In fourth, because the ETT channel 116 is located in the handle 112, the shape of the handle 112 is not altered when the ETT 406 is loaded in the ETT channel 116, making it easy for a healthcare practitioner to manipulate the laryngoscope 100 during insertion.

In fifth, after an endotracheal tube 406 has been positioned through the vocal cords, the laryngoscope 100 can be separated from the endotracheal tube 406 through the slit 126. Thus, the laryngoscope 100 can be removed from a patient without disturbing the endotracheal tube 406 which may remain positioned as needed and may continue providing ventilation to the patient.

In sixth, it is possible to position the endotracheal tube 406 into the ETT channel 116 prior to inserting the laryngoscope into an oral cavity as the endotracheal tube 406 being positioned inside the ETT channel 116 does not interfere with using the laryngoscope for lifting the epiglottis.

In some preferred embodiments of the laryngoscope according to this disclosure, the ETT channel 116 may contain a guide groove 118. When present in some preferred embodiments, the guide groove 118 is a groove or recess in the wall 109 of the ETT channel 116, one embodiment of which can be seen in a cross-sectional view of FIG. 16. The guide groove 118, when present, may start with an opening 118P at or near the proximal end 112P of the handle 112. The guide groove 118 may continue through the length of at least a portion of the handle 112 and then in some embodiments, it may further continue through at least a portion of the length of the blade 114, as shown for example in FIG. 24. The guide groove 118 in some preferred embodiments ends with an opening 118D at or near the distal end 114D of the blade 114. A depth of the guide groove 118 may vary, but typically it is compatible with a diameter of a guide tool, e.g., a bougie 208 such as that the bougie 208 can be positioned in the guide groove 118. The guide groove 118 may be formed in the wall of ETT channel 116 and accordingly, the guide groove 118 opens in some preferred embodiments into the lumen (the passageway) of ETT channel 116 such that the bougie 208 can be easily moved from the guide groove 118 into the lumen of the ETT channel 116 or the bougie 208 can be secured back in the guide groove 118, as may be needed.

Figures 20, 21, 22:
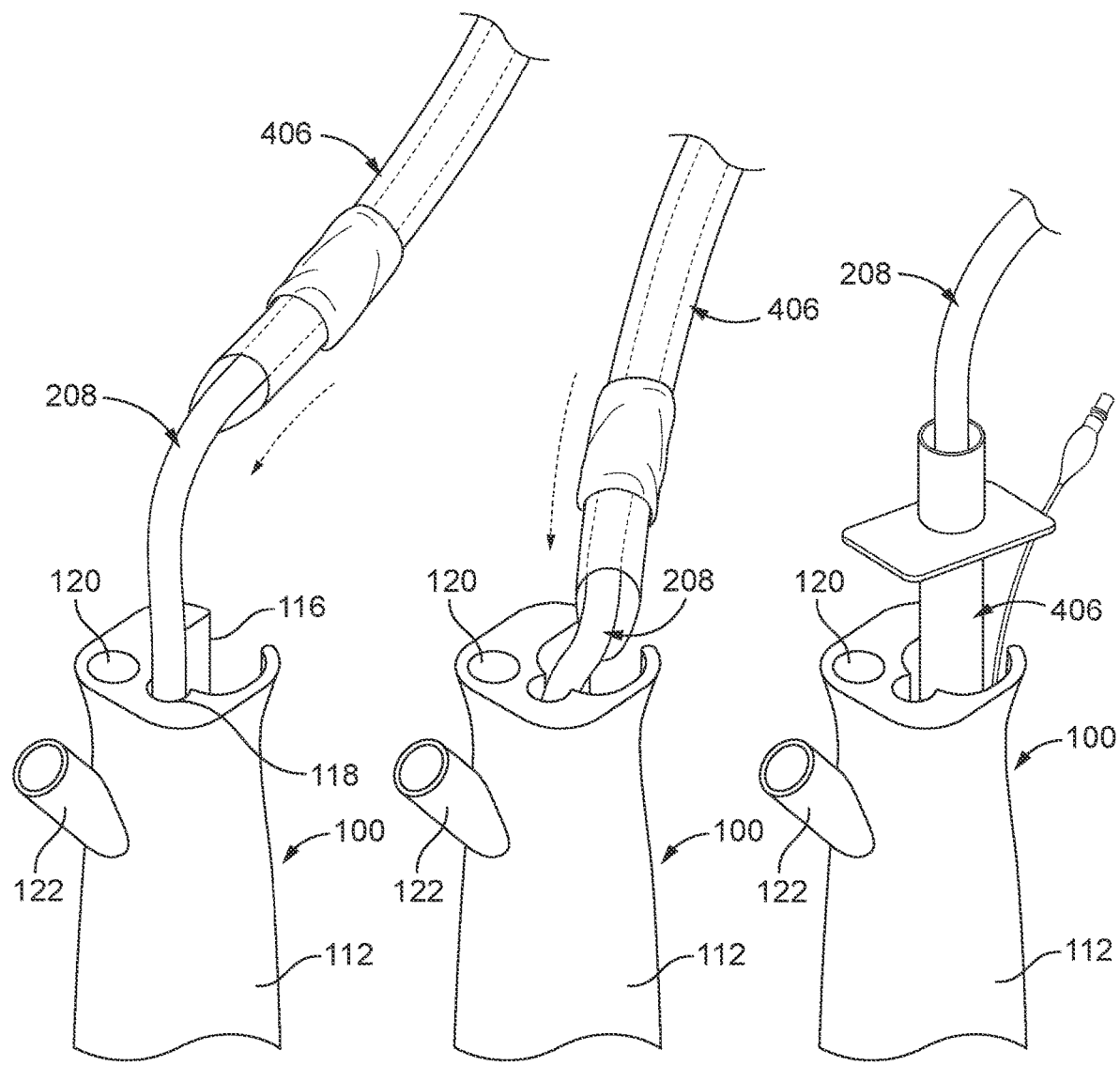
FIG. 20 depicts a proximal region of the handle of the laryngoscope 100 with a bougie positioned in a guide groove.
FIG. 21 depicts the assembly of FIG. 20 and further depicting an endotracheal tube being guided with the bougie into an ETT channel.
FIG. 22 depicts the assembly of FIG. 21 after the endotracheal tube has been fully loaded into the ETT channel.

As is shown in FIG. 20, after the laryngoscope 100 has been placed in a patient and the larynx has been opened, a bougie 208 can be placed into an endotracheal tube 406. The bougie 208 can be then extended distally from the distal end of the endotracheal tube 406. The bougie 208 can then be placed in the guide groove 118 of the laryngoscope 100 and is used for guiding and docking the endotracheal tube 406 into ETT channel 116, as shown for example, in FIGS. 21 and 22. Thus, one of the functions for the guide groove 118 is to serve as a docking means for delivering an endotracheal tube through ETT channel 116 and into a correct position in the trachea.

In the embodiments without the guide groove 118, the guide tool, such as the bougie 208, may be placed directly into ETT channel 116.

Some preferred embodiments of the laryngoscope according to this disclosure include a suction/camera channel 120 which opens with a proximal end opening 120P at or near the proximal end 112P of the handle 112. The suction/camera channel 120 can be referred in this disclosure as the suction channel 120 or simply as the channel 120.

The proximal end opening 120P leads into the channel 120 which is preferably a passageway formed in the body 113 of the handle 112. The channel 120 may be continued as a passageway formed in the body 117 of the blade 114. The suction channel 120 may open with a distal end opening 120D at or near the distal end 114D of the blade 114. In some embodiments, the distal end opening 120D of the suction channel 120 can open directly into the ETT channel 116.

Figure 17:
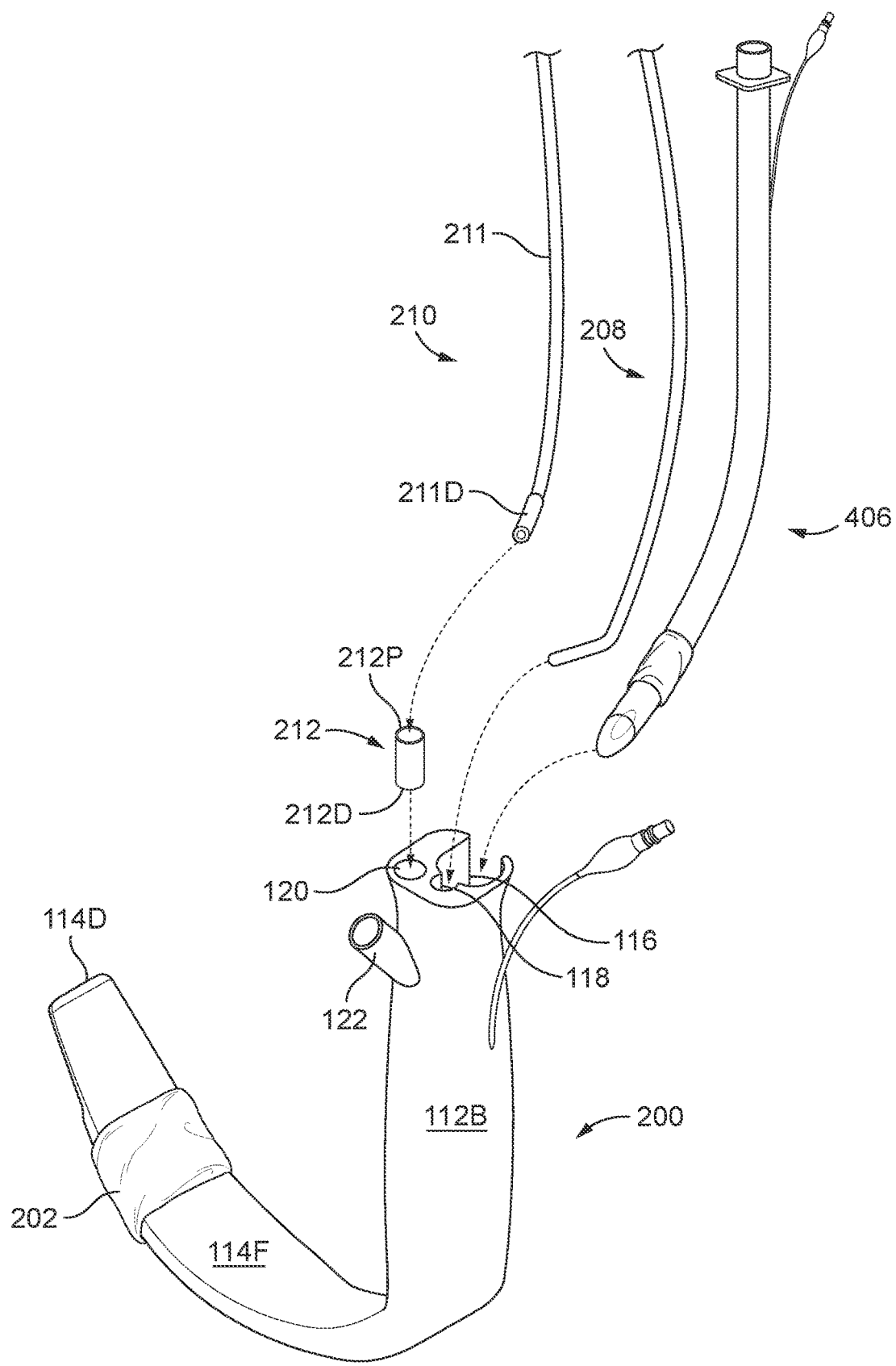
FIG. 17 depicts the laryngoscope with a cuff of FIG. 12 being assembled with an endotracheal tube, a bougie and a camera.
Figure 18:
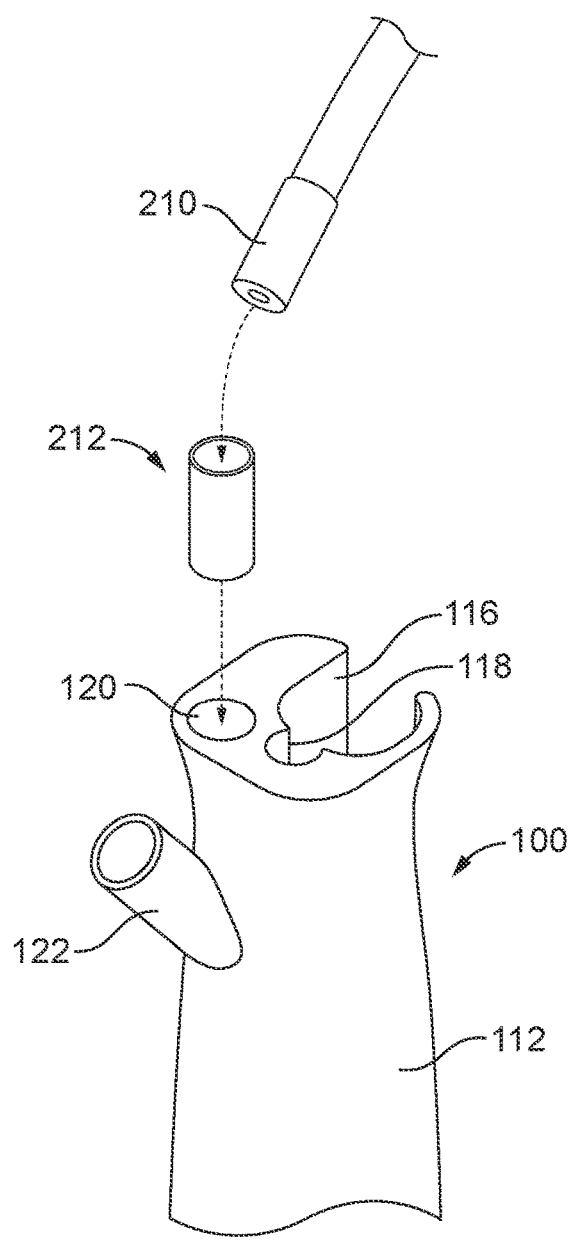
FIG. 18 depicts a proximal region of the handle of the laryngoscope 100 according to this disclosure, a camera adapter and a camera.
Figure 19:
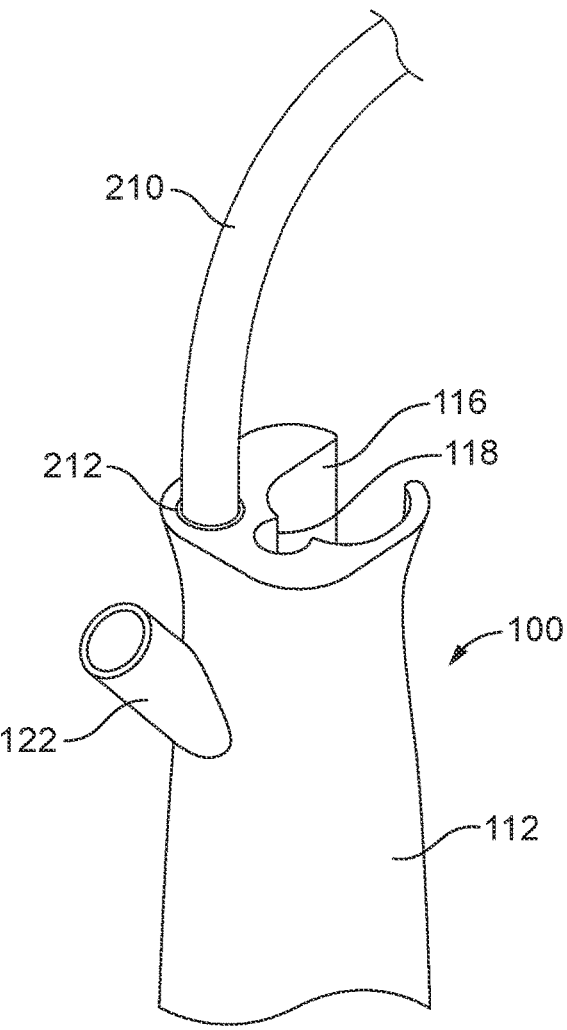
FIG. 19 depicts the camera of FIG. 18 being placed into the laryngoscope of FIG. 18 through the camera adapter of FIG. 18.

Preferably, the channel 120 has a diameter compatible with housing a camera such that a camera 210 can be positioned through the proximal opening 120P into the channel 120, as shown for example, in FIG. 17. The camera 210 can extend distally from the distal end opening 120D of the channel 120. Because a diameter of the suction channel 120 is larger than a diameter of the camera 210, the camera 210 can slide in the suctions channel 120 along the proximal-distal 120P/120D axis of the channel 120.

The laryngoscopes according to this disclosure can be used with any cameras (videoscopes) 210 which are typically used in laryngoscopy and/or endoscopy. Suitable cameras include those which transmit real-time video images, preferably 2.0 megapixel or higher, including those with a WiFi capability and preferably compatible for wireless transmission to a smart phone, tablet and/or a computer. In alternative or in addition to wireless transmission, suitable cameras include those which can be connected to a monitor with a cable.

In some embodiments, a camera can be battery-operated. Suitable cameras include a charge-coupled device (CCD) located at the distal end, 211D, of the scope (wand) 211 of the camera 210. Suitable cameras also include fiberscopes and preferably fiberscopes with a probe of adjustable length.

A camera can be further equipped with a light source, the light intensity of which is preferably adjustable. When a camera is positioned in the channel 120, it can provide real-time images of patient's glottis, larynx and/or vocal cords. Accordingly, placement of the laryngoscope 100 as well as intubation with an endotracheal tube can be performed under continuous visualization.

Figure 11:
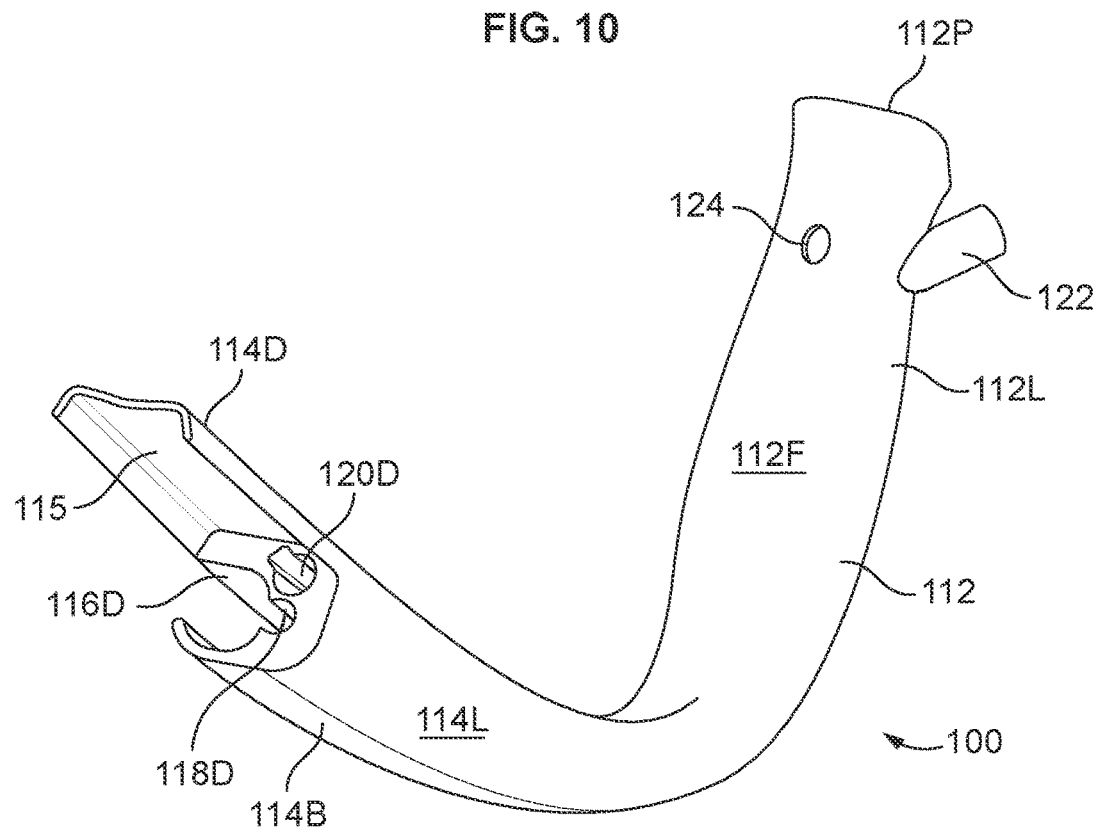
FIG. 11 depicts another side perspective view of the laryngoscope of FIG. 10.
Figure 15:
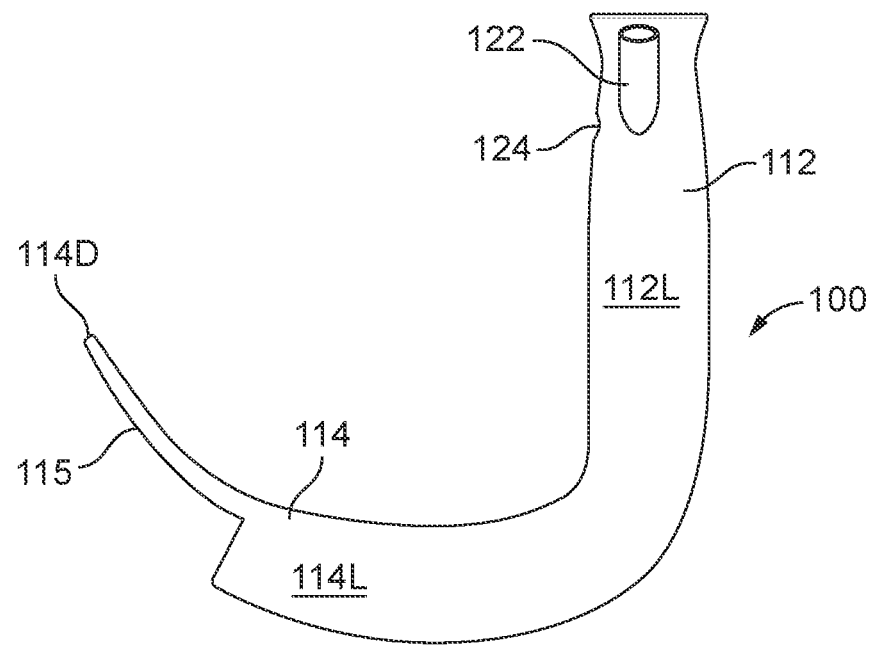
FIG. 15 is a side-view of the laryngoscope of FIG. 10.

As can be seen for example, in FIG. 11 and FIG. 15, the flange 115 may extend distally over the distal end opening of the channel 120 at least in some preferred embodiments. The flange 115 may protect, if necessary, the camera 210 during insertion of the laryngoscope 100. However, and if necessary, the camera 210 can be extended further from the distal end opening 120D of the channel 120. In some applications, the camera 210 can be extended distally to the flange 115. Accordingly, the camera 210 can provide continuous visualization during insertion of the laryngoscope 100. The camera 210 can slide distally and proximally in the channel 120, providing visualization of the distal end 114D of the blade 114. The camera 210 can be also moved further distally to provide visualization of patient's tissues distally from the distal end 114D.

As can be appreciated in FIGS. 11, 15 and 16, the channel 120 is preferably positioned in the body of the laryngoscope 100 relative to the ETT channel 116 such that the camera 210, when extending from the distal end opening 120D of the channel 120 can visualize the distal end 406D of the endotracheal tube 406 positioned in the ETT channel 116 with the distal end 406D of the endotracheal tube 406 extending distally from the distal end 116D of the ETT channel 116.

In some embodiments, the channel 120 is positioned near or substantially near the mid-line of the body of the laryngoscope 100. In some other embodiments, the channel 120 is positioned laterally to the mid-line of the body of the laryngoscope 100.

Because of the preferred relative positioning of the ETT channel 116 and the channel 120 in the body of the laryngoscope 100 such that the distal end opening 120D of the channel 120 is in the proximity to the distal end 116D of the ETT channel 116, both being located at or near the distal end 114D of the blade 114, manipulations with a bougie 208 and insertion of the endotracheal tube 406 can be conducted under continuous visualization by the camera 210 when the camera 210 is positioned in the channel 120. It should be further noted that the ETT channel 116 can be also used for housing a camera. In some embodiments, the laryngoscope according to this disclosure can be used with two different cameras, one positioned in the channel 120 and another one positioned in the ETT channel 116.

Because a camera can be positioned in the separate channel 120 separated by the wall from the ETT channel 116, the camera can be removed from the laryngoscope 100 while the laryngoscope 100 and the endotracheal tube 406 remain positioned in a patient. In alternative, a camera can be re-introduced back into the channel 120 at any time during examination and intubation and while the laryngoscope 100 remains positioned in a patient. There is no need to remove the laryngoscope assembly from the patient before a camera can be assembled with the laryngoscope.

At least in some preferred embodiments, the handle 112 may further comprise a connector 122 positioned on the handle 112. The connector 122 is a conduit (a tube) extending from the body 113 and is attached to the body 113. The connector 122 is preferably a tube having a wall which encloses a lumen 123 which opens through an opening in the body 113 into the channel 120. The connector 122 can be used for connecting the laryngoscope 100 to an oxygen, suction and/or vacuum source. The connector 122 may comprise a valve or some other means, e.g., a cap, that can regulate opening and closing of the lumen 123 in the connector 122.

When in operation with a vacuum source, the connector 122 can be used for aspirating bodily fluids (e.g., blood, vomit and/or mucous) through the channel 120. This procedure can be conducted under continuous visualization by a camera positioned in the channel 120 and/or in the ETT channel 116. Thus, at least in some preferred embodiments, the channel 120 has a dual function: it can carry a camera and it can also function as a suction channel.

In some embodiments, the handle 112 may comprise a suction control port 124 located on the handle 112, preferably in the proximal portion of the handle 112 and even more preferably on the front surface 112F in the proximal portion of the handle 112. The suction control port 124 provides a lumen in the body 113 leading into the channel 120 such that air can enter the channel 120 through the suction control port 124.

One of the functions for the suction control port 124 is to control the air pressure inside the suction lumen 122. This function can be accomplished by opening and closing the suction control port 124.

When suction is needed in order to clear an airway from bodily secretions, a suction catheter (not shown) may be connected to a suction/vacuum source (not shown) and to the laryngoscope 100 through the connector 122. Secretions are then aspirated into the channel 120 from the distal end 120D and removed from the channel 120 through the connector 122.

When open, the suction control port 122 supplies air to the channel 120. Accordingly, vacuum in the channel 120 is released at least partially through the suction control port 124. This decreases suction through the channel 120 at least partially.

A healthcare professional may close the suction control port 124 with a finger, a piece of tape and/or a suction control port may be fitted with a stopper/plug/lid (not shown). If no suction is needed or only if minimum suction is needed, the suction control port 122 may be kept open. In order to increase suction and aspiration of bodily secretions through the channel 120, the suction control port 124 may be closed with a finger or with a stopper/plug/lid (not shown).

In some preferred embodiments, the suction control port 124 is positioned on the handle 112 proximally to the connector 122. In some preferred embodiments, the suction control port 124 is positioned on the front surface 112F of the handle 112 and proximally to the connector 122 positioned on the left flanking surface 112L or the right flanking surface 112R.

Figure 12:
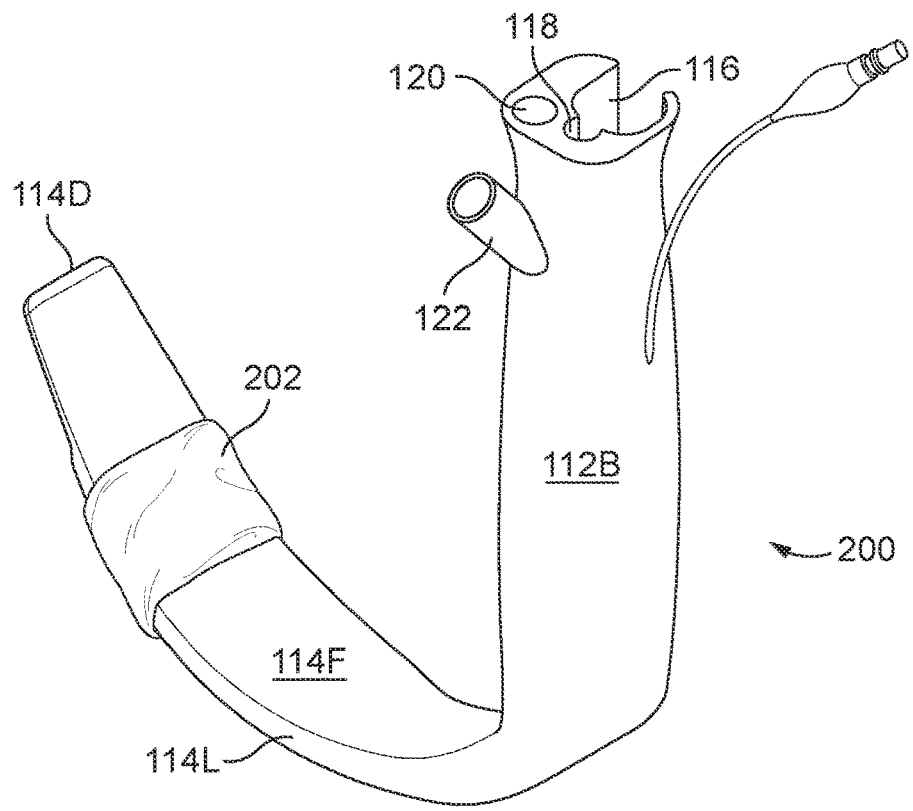
FIG. 12 is a perspective view of another embodiment of a laryngoscope with a cuff according to this disclosure.
Figure 13:
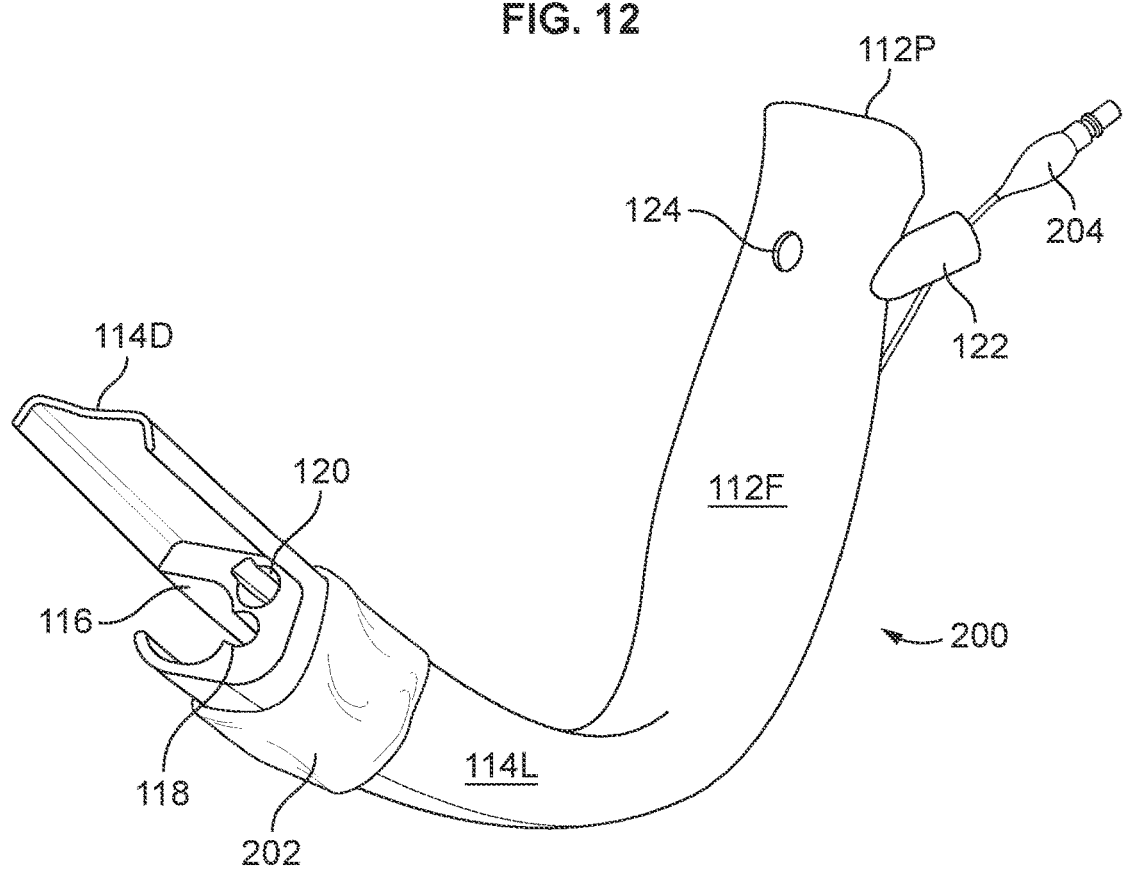
FIG. 13 is another side perspective view of the laryngoscope of FIG. 12.
Figure 14:
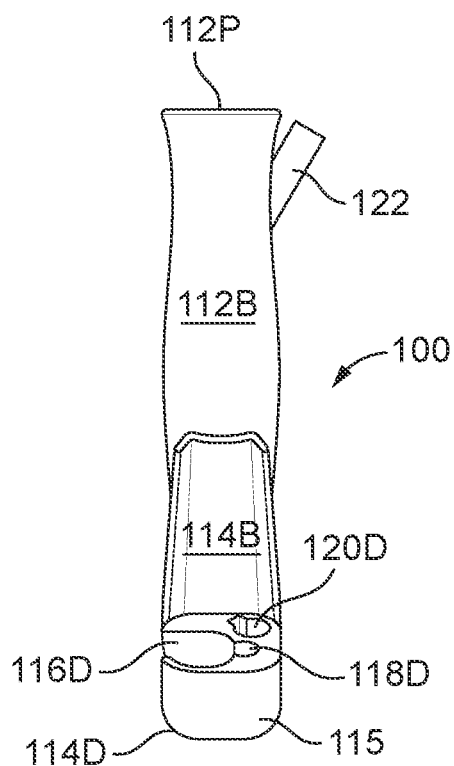
FIG. 14 is a top-view of the back surface of the laryngoscope of FIG. 10.

Referring to FIGS. 12, 13, and 17, it shows an alternative embodiment of a laryngoscope according to this disclosure, generally 200. The laryngoscope 200 may have the same structure as the laryngoscope 100 and it may contain some of the same elements as were described in connection with the laryngoscope 100.

The laryngoscope 200 comprises the handle 112 attached to the blade 114 as was described in connection with the embodiments of the laryngoscope 100. However, the laryngoscope 200 further comprise a cuff 202 attached at the distal portion of the blade 114, as can be best seen in the FIGS. 12 and 13. In some embodiments, the cuff 202 is non-inflatable, while in some other embodiments, the cuff 202 is inflatable and can be inflated with means 204.

As can be best seen in FIG. 13, the cuff 202 in some embodiments is attached to the blade 114 in its distal portion, wherein the cuff 202 is located proximally to the distal end 114D of the blade 114 such that the distal end opening 116D for the ETT channel 116 and the distal end opening 120D of the channel 120 open distally to the cuff 202.

In some embodiments where the slit 126 is present, the cuff 202 may be attached to the blade 114 such that the cuff 202 does not cover the slit 126. In other embodiments, the cuff 202 may wrap around the blade 114 such that the cuff 202 also wraps around the slit 126.

When in use, after the laryngoscope 200 has been positioned in a patient which can be conducted under continuous visualization with a camera positioned for example in channel 120, the cuff 202 can be inflated and a patient can be ventilated while a healthcare practitioner is working for example on positioning an endotracheal tube and/or performing other tasks necessary for examining and managing an airway.

In yet another aspect, the present disclosure provides an embodiment for a camera adopter, generally 212. As can be seen in FIG. 17, the camera adopter 212 is preferably a substantially cylindrical body, a wall of which is encircling a central lumen. The camera adopter 212 is insertable into and removable from a lumen of the channel 120 through the proximal end opening 120P. The camera adapter 212 has a distal end 212D and a proximal end 212P and a length between the distal end 212D and the proximal end 212P. The camera adapter 212 may have a sealed window located at the distal end 212D. In some embodiments, the camera adapter 212 can fit over the camera 210 for example as shown in embodiments of FIGS. 17, 18 and 19. The camera adapter 212 can be used for protecting the camera 210 from the exposure to bodily fluids and damage while the camera 210 is in use with any laryngoscope embodiments of this disclosure, e.g., 10, 100, 200, 500 or 700.

In yet another embodiment and referring to FIGS. 25, 26, 27 and 28, the present disclosure provides a channel adapter 300 having in some embodiments a substantially conical body 302 formed by a wall that encloses a lumen 303. The body 302 has a distal end 302D and a proximal end 302P and a length between the distal end 302D and the proximal end 302P.

Figure 27:
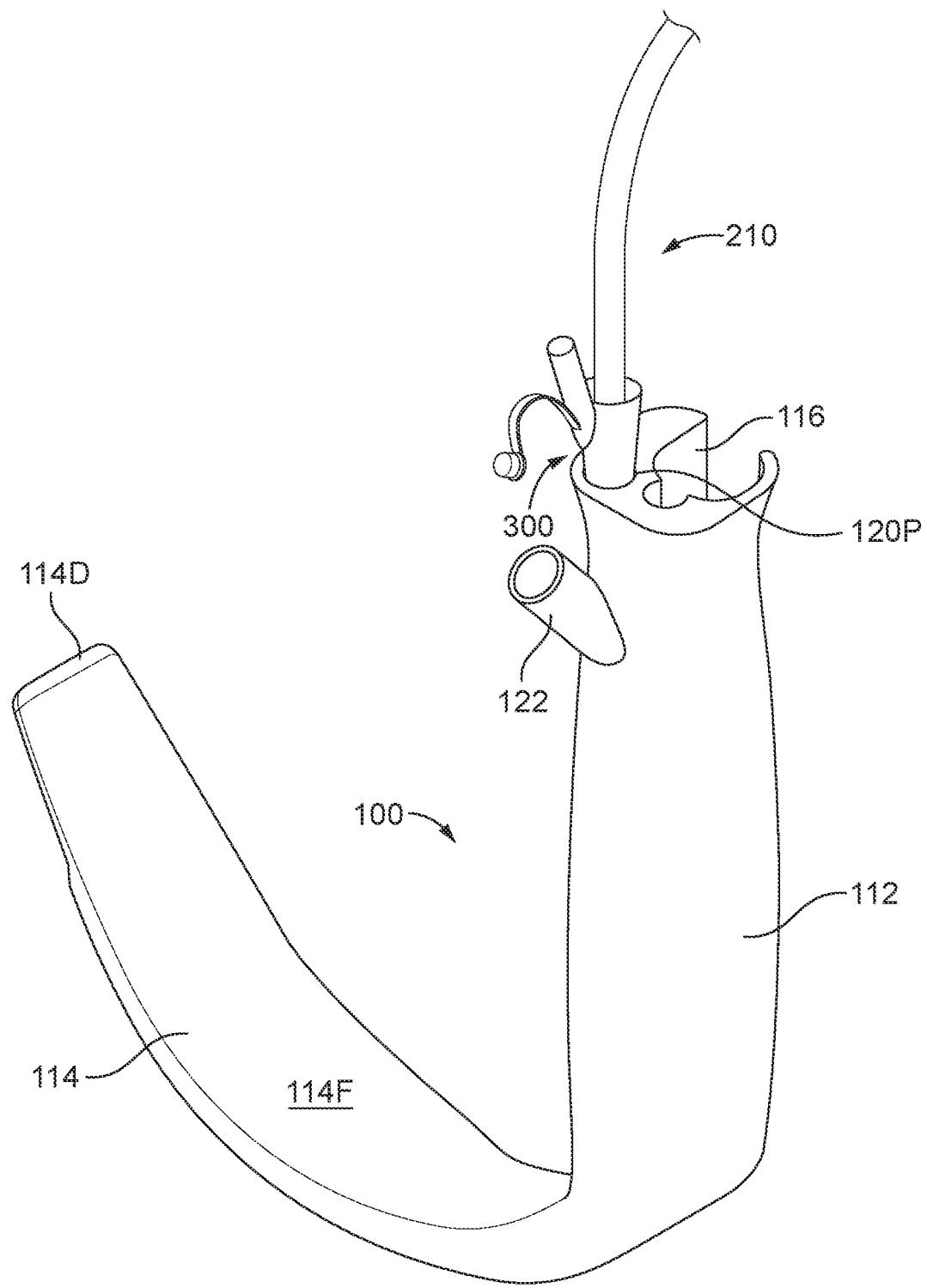
FIG. 27 is a perspective view of an assembly of the laryngoscope of FIG. 1 being assembled with a camera through the adapter of FIG. 25.
Figure 28:
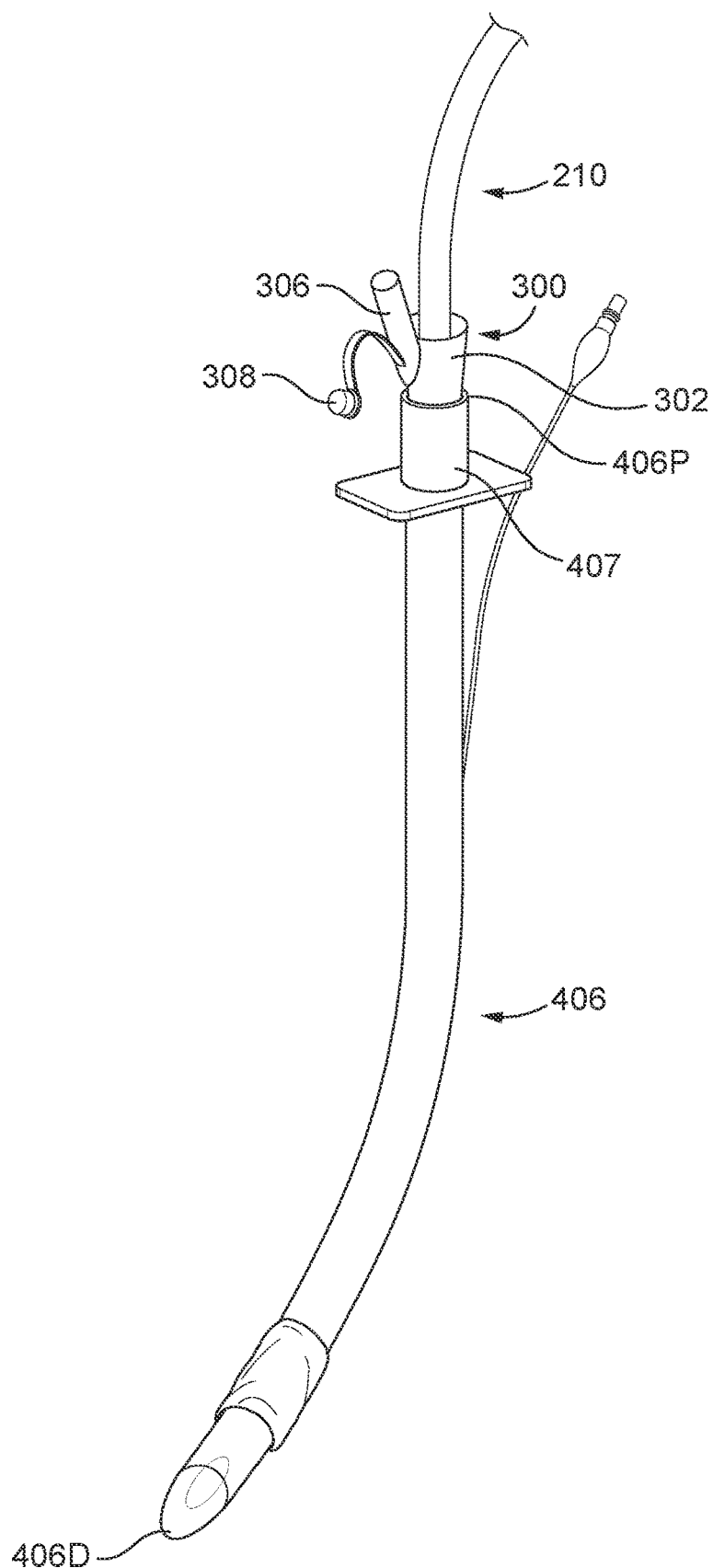
FIG. 28 depicts an assembly of an endotracheal tube with a camera via the adapter of FIG. 25.

The body 302 has a first diameter (d1) at its distal end 302D and the body 302 has a second diameter (d2) at its proximal end 302P, wherein the first diameter (d1) is preferably smaller than the second diameter (d2), and wherein the first diameter (d1) is smaller than a diameter at the proximal end 120P of the channel 120, and wherein the second diameter (d2) is larger than the diameter of the proximal end 120P of the channel 120. Accordingly, a distal portion of the channel adapter 300 is insertable into the channel 120. The distal portion of the channel adapter 300 fits tightly into the proximal opening 120P of the channel 120, but the proximal portion of the adapter 300 remains outside the channel 120, as shown for example in FIG. 27. The lumen 303 of the adapter 300 is compatible with the camera 210. The camera 210 can be placed into the lumen 303 of the adapter 300 and then assembled with a laryngoscope, for example, as shown in FIG. 27, or with an endotracheal tube 406 as shown, for example, in FIG. 28 by inserting the distal end 302D of the channel adaptor 300 into the opening 120P of the channel 120.

The channel adapter 300 may further contain at least one port 304 located on the wall of the body 302. The port 304 serves as an ingress into the lumen 303. One of the functions for the port 304 is to control air pressure in the channel 120 or in any other tube with which the channel adapter 300 is assembled. The channel adapter 300 may further comprise a conduit 306 formed as a hollow tube attached to and extending from the wall of the body 302. The conduit 306 encloses a lumen 310 which connects with the lumen 303 through an opening in the wall of the body 302. The conduit 306 can be used for connecting the channel adapter 300 to an air/vacuum source. When not in use, the lumen 310 of the conduit 306 can be closed with a lid 308 which may be attached in some embodiments to the wall of the conduit 306 with a lid strap 309.

Figures 29, 30:
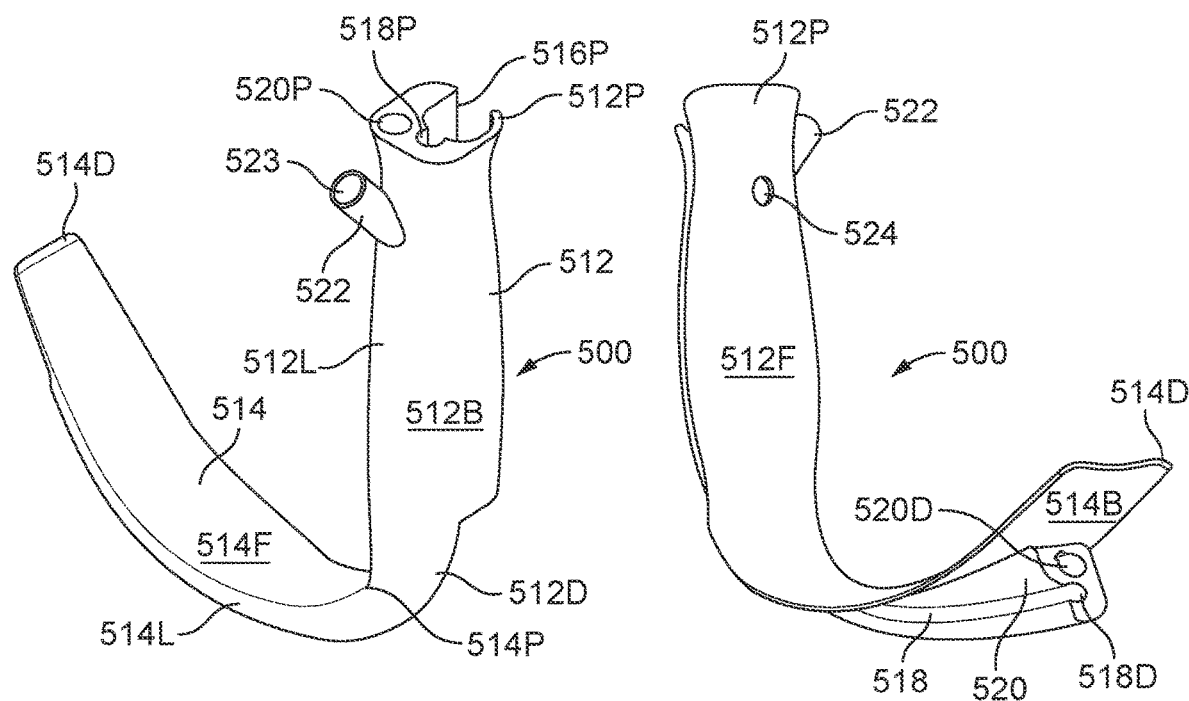
FIG. 29 depicts another embodiment of a laryngoscope according to this disclosure in which an ETT channel is located in the handle.
FIG. 30 is a perspective view of the laryngoscope of FIG. 29, showing the back surface of the blade.

Referring to FIGS. 29 and 30, the present disclosure provides yet another embodiment for a laryngoscope, generally 500. Just like other laryngoscopes of this disclosure, the laryngoscope 500 comprises the handle 512 attached to the blade 514, as was described in connection with the embodiments of the laryngoscope 100.

Preferably, the handle 512 has a substantially tubal body having a length between a proximal end 512P and a distal end 512D. It should be noted that while in one embodiment, the handle 512 has a substantially tubal body, any other shapes typically used for handles can be also suitable. The shape and the length of the handle 512 can be adjusted as needed in order to facilitate a sufficient grasp by a healthcare professional for manipulating the handle 512 during insertion and while conducting examination and/or intubation.

The handle 512 has a front surface 512F and the opposite back surface 512B. Between the front surface 512F and the back surface 512B, the handle 512 a flanking surface, the right flanking surface 512R and it opposite, the left flanking surface 512L.

In some embodiments, a width of the handle 512 which can be defined as the width of the front surface 512F from the left flank 512L to the right flank 512R is substantially same as a width of the blade 514 which can be measured as the width of the blade front surface 514F from the left flank 514L to the right flank 514R. In other embodiments, the width of the handle 512 is less than the width of the blade 514 and the blade 514 is wider (broader)a than the handle 512.

The blade 514 may be curved and is preferably adopted to fit with the contour of a human larynx such that when the laryngoscope 500 is in use, the blade 514 is insertable into the human larynx and the blade 514 can be used to lift the epiglottis. The blade 514 can be introduced into an oropharynx by manipulating the handle 512 which remains substantially extended out of the mouth. The blade 514 is shaped such that it can extend to the hypopharynx and glottic structures. The blade 514 is sufficiently rounded to pass over the patient's tongue.

The blade 514 has a distal end 514D and a proximal end 514P. The handle 512 is attached at its distal end 512D to the proximal end 514P of the blade 514. In at least some embodiments, the blade 514 is attached to the handle 512 at an angle α such that the laryngoscope 500 is J-shaped. The angle α can be optimized as needed, and preferably it can be at any value between 30 and 150 degrees. Other values can be also suitable. The angle α is optimized based on the angle needed for performing functions such as passing over the tongue and lifting the epiglottis with as little manipulation of the head and the neck as possible. In some embodiments, the blade 514 is wider (broader) than the handle 512.

The blade 514 has a back surface 514B and the opposite front surface 514F. A healthcare professional may grasp the handle 512 and introduce the blade 514 into the oropharynx of a patient by manipulating the handle 512 in order to obtain a view of the vocal cords and the glottis and while attempting to gain access to the patient's airway. After insertion is successfully completed, the front surface 514F of the blade 514 is positioned toward the patient's front, while the back surface 514B is positioned toward the patient's back.

Just like other laryngoscope embodiments in this disclosure, the laryngoscope 500 contains a suction/camera channel 520, the structure and function of which is substantially similar to the channel 120. The channel 520 is a passageway in the body of the handle 512 that is further continued through the blade 514. The channel 520 starts with a proximal end opening 520P at or near the proximal end 512P of the handle 512. The channel 520 ends with a distal end opening 520D located at or near the distal end 514D of the blade 514. The channel 520 may further be connected to a connector 522. Functions and a location of the connector 522 on the handle 512 are the substantially the same as for the connector 122 of the handle 112. The handle 512 may further comprise a suction control port 524, functions and a location of which are substantially the same as those for the suction control port 124 on the handle 112. The suction control port 524 controls air pressure in the channel 520. The channel 520 can be further used for housing a camera which can extend distally from the opening 520D and collect images in real time distally to the distal end 514D of the laryngoscope 500.

The laryngoscope 500 contains an ETT channel 516, the structure of which is different from the ETT channel 116. The ETT channel 516 is a passageway in the body of the handle 512. The ETT channel 516 starts with a proximal end 516D located at or near the proximal end 512P of the handle 512. The ETT channel 516 ends with a distal end opening 516D at or near the distal end 512D of the handle 512. In some alternative embodiments, the distal end opening 516D may open the ETT channel 516 proximally to the distal end 512D of the handle 512. An endotracheal tube can be placed into the ETT channel 516. A distal end of the endotracheal tube can extend from the distal end 516D of the ETT channel 516. In some preferred embodiments, the ETT channel 516 also contains a slit along at least a portion of its length such that an endotracheal tube can be placed and removed from the ETT channel 516 through the slit similarly as described in connection with the slit 126 shown in FIG. 24. Preferably, the ETT channel 516 ends proximally to the proximal end 514P of the blade 514. Accordingly, a distal portion of an endotracheal tube which is extending from the distal end opening 516D of the ETT channel 516 can be aligned over the back surface 514B of the blade 514. This allows for visualization of the endotracheal tube with a camera extending distally from the channel 520. All procedures can be performed under continuous visualization and suction can be used on demand if/when needed by regulating a pressure through the suction control port 524.

Because the ETT channel 516 is located in the body of the handle 512, the shape of the handle is suitable for manipulations without concerns for damaging or dislocating an endotracheal tube as the ETT channel protects the endotracheal tube from damage and/or deformation. However, because there is no internal ETT channel present in the blade 514, as the endotracheal tube extends out from the ETT channel 516 at or near the distal end 512D of the handle 512, the blade 514 can be made substantially flat or at least flatter than in conventional channel laryngoscopes. It is believed that reducing the thickness of the blade 514 may improve its function for lifting the epiglottis and protecting patient's tissues. In the laryngoscope embodiment 500, the laryngoscope comprises a guide groove 518, functions and a location of which are similar to those of the guide groove 118. The guide groove 518 is preferably a recess in the wall of the ETT channel 516 and then it may continue as a recess on the external wall of the channel 520 such as that a tool, such as a bougie, can be placed in the groove 518 for guiding an endotracheal tube placed in the ETT channel 516.

Figures 31, 32:
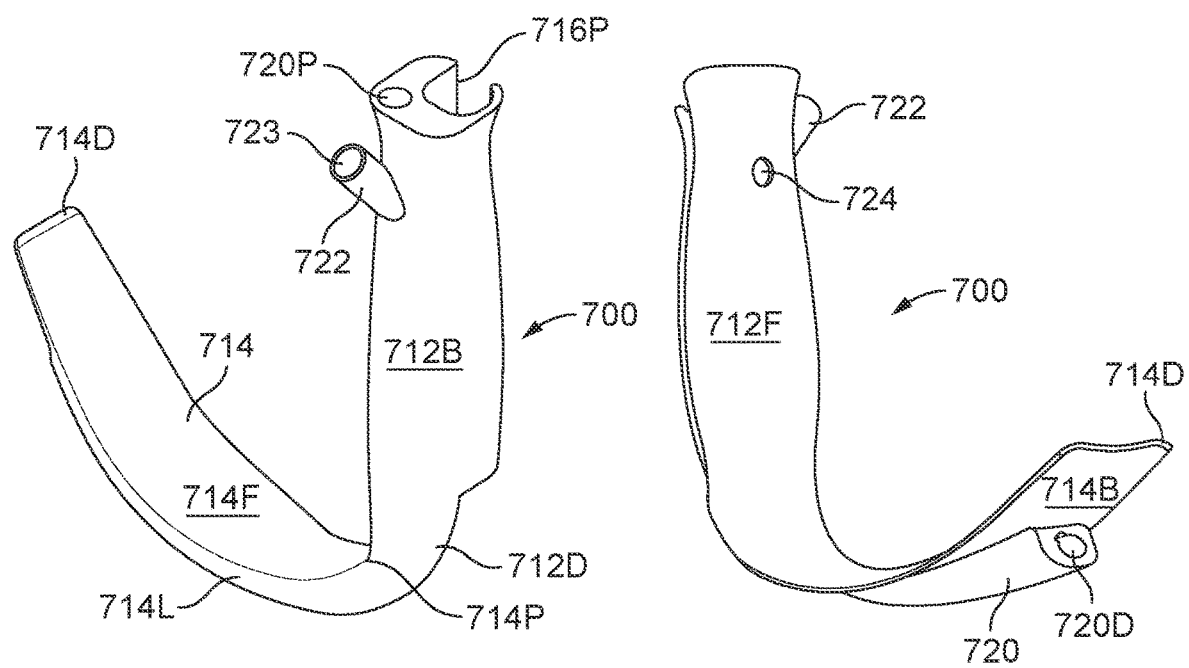
FIG. 31 depicts another embodiment of a laryngoscope according to this disclosure in which an ETT channel is located in the handle.
FIG. 32 is a perspective view of the laryngoscope of FIG. 31, showing the back surface of the blade.

Referring to FIGS. 31 and 32, the present disclosure provides yet another embodiment for a laryngoscope, generally 700. Just like other laryngoscopes of this disclosure, the laryngoscope 700 comprises the handle 712 attached to the blade 714, as was described in connection with the embodiments of the laryngoscope 100 and/or 500. FIG. 31 depicts the back surface 712B of the handle 712 and the front surface 714F and the left flank 714L of the blade 714. FIG. 32 depicts the front surface 712F of the handle 712 and the back surface 714B of the blade 714.

An ETT channel 716 has substantially the same structure and functions as was described in connection with the ETT channel 516. The channel 716 starts with a proximal end 716P at or near the proximal end 712P of the handle 712. The channel 716 opens with a distal opening (not shown in FIG. 31 or 32) at or near the distal end 712D of the handle 712. In some preferred embodiments, the channel 716 can open with a distal end opening proximally to the distal end 712D such that an endotracheal tube can be placed in the ETT channel 716 and aligned with the blade 714 wherein the ETT extends out the distal end 712D and is aligned externally to the blade 714.

In the laryngoscope embodiment 700, a suction/camera channel 720 has substantially the same structure and functions as was described in connection with the channel 520. A distal end opening 720D of the channel 720 is preferably located under the back surface 714B of the blade 714. Preferably, the channel 720 ends proximally to the distal end 714D of the blade 714, such as the thickness of the blade 714 at the distal end 714D is as flat as possible and it serves as a flange protecting a camera when the camera is inserted into the channel 720 and the camera extends distally from the channel 720.

The suction control port 724 has the same structure and functions as was described in connection with the suction control ports 124 and 524. A connector 722 with a lumen 723 has substantially the same location, functions and structures as was described in connection with the connector 122. Unlike the embodiment of laryngoscope 500, the laryngoscope 700 does not contain a guide groove.

Figure 33:
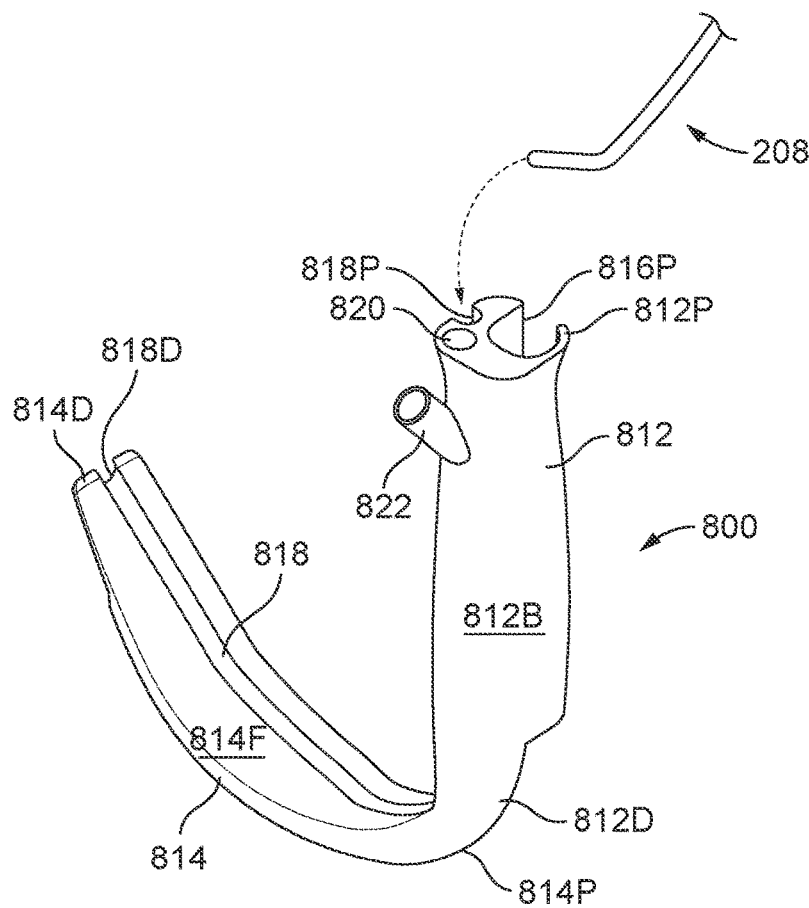
FIG. 33 is a perspective view of another embodiment of a laryngoscope according to this disclosure.
Figure 34:
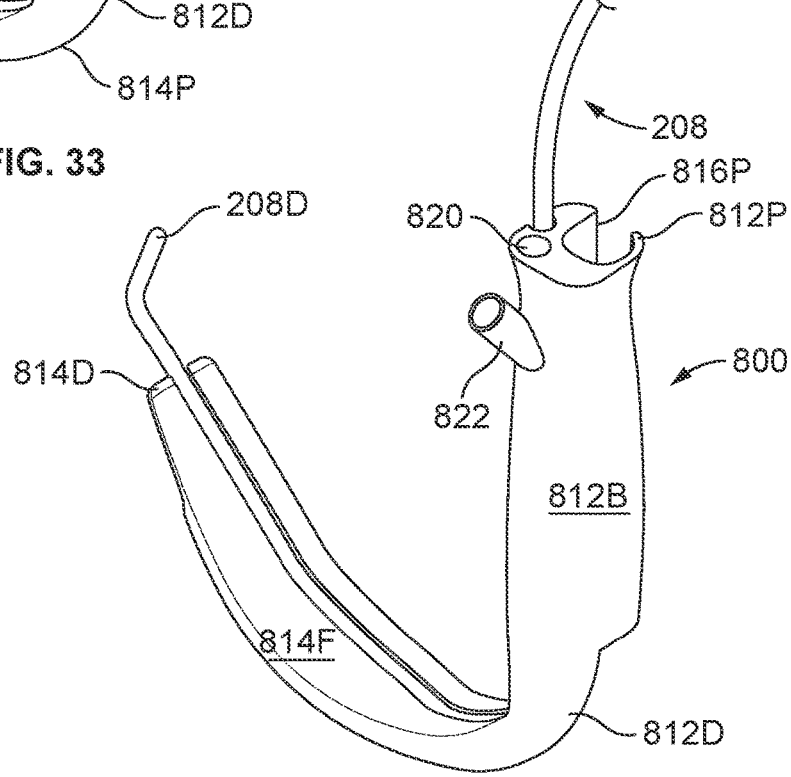
FIG. 34 depicts the laryngoscope of FIG. 33 assembled with a bougie.

Referring to FIGS. 33 and 34, they depict another embodiment for a laryngoscope according to this disclosure, generally 800. Just like other laryngoscopes of this disclosure, the laryngoscope 800 comprises the handle 812 attached to the blade 814, as was described in connection with the embodiments of the laryngoscope 100, 500 and 700. FIG. 33 depicts the back surface 812B of the handle 812 and the front surface 814F and the left flank 814L of the blade 814. FIG. 34 depicts a bougie 208 assembled with the laryngoscope 800.

The laryngoscope 800 contains an ETT channel 816, the structure of which is similar to that of the ETT channels 516 and 716. The channel 816 starts with a proximal end 816P at or near the proximal end 812P of the handle 812. The channel 816 opens with a distal opening (not shown in FIG. 33 or 34) at or near the distal end 812D of the handle 812. In some preferred embodiments, the channel 816 can open with a distal end opening proximally to the distal end 812D such that an endotracheal tube can be placed in the ETT channel 816 and aligned with the blade 814 wherein the ETT extends out the distal end 812D and is aligned externally to the blade 814.

In the laryngoscope embodiment 800, a suction/camera channel 820 has substantially the same structure and functions as was described in connection with the channel 520. A distal end opening 820D of the channel 820 is preferably located under the back surface 814B of the blade 814. Preferably, the channel 820 ends proximally to the distal end 814D of the blade 814, such as the thickness of the blade 814 at the distal end 814D is as flat as possible and it serves as a flange protecting a camera when the camera is inserted into the channel 820 and the camera extends distally from the channel 820.

A connector 822 with a lumen has substantially the same location, functions and structures as was described in connection with the connector 122.

Unlike other embodiments, the laryngoscope 800 contains a guide groove 818 formed as a recess (notch) on the surface for at least a portion of the handle 812 length. In the embodiment of FIG. 33, the guide groove 818 starts with a proximal end 818P located at or near the proximal end 812P of the handle 812. In the embodiment of FIG. 33, the guide groove 818 is located on the front surface 812F of the handle 812. In other embodiments, the guide groove 818 may be located on the back surface 812B or on one of the flank surfaces 812L or 812R.

In the embodiment of FIG. 33, the guide groove 818 continues as a recess (notch) on the front surface 814F of the blade 814 for at least a portion of the blade 814 length. The guide groove 818 ends with a distal end 818D located at or near the distal end 814D of the blade 814. In other embodiments, the guide groove 818 may be formed on the back surface 814B of the blade 814 or in one of the flanks 814L or 814R.

A depth of the guide groove 818 is compatible with a bougie 208 which can be placed in the guide groove 818 as shown in FIG. 34.

In further embodiments, any of the laryngoscopes 100, 200, 500, 700 or 800 may further comprise at least one camera/tool channel 28 as was discussed in connection with laryngoscope embodiment 10.

In yet another aspect, the present disclosure provides methods for gaining access to patient's airway with the laryngoscope according to this disclosure, as may be needed in medical emergency and/or in order to facilitate endotracheal intubation during certain surgical procedures, in general anesthesia and/or under other circumstances when a patient cannot breathe unassisted or examination of patient's airway may be needed. In some of these methods, a healthcare professional may position at least one camera attached to a cable or wand, e.g., the camera 210, in the suction/camera channel and/or the ETT channel of the laryngoscope 10, 100, 200, 500, 700, or 800 and then further optionally inserting a bougie, e.g., the bougie 208, in the ETT channel and preferably, in the guide groove if present. Certain embodiments of the methods may further include positioning an endotracheal tube, e.g., the endotracheal tube 406, in the ETT channel. Some of the technical advantages for the laryngoscopes according to this disclosure is that the ETT channel is located inside the laryngoscope handle, protecting an endotracheal tube from deformation and/or damage and providing the opportunity to assemble an endotracheal tube with the laryngoscope before a procedure starts.

A healthcare practitioner can then introduce the blade of the laryngoscope according to this disclosure into the oropharynx by manipulating the handle and the bougie 208. The healthcare practitioner can then advance the blade into the hypopharynx and lift the epiglottis. All these procedures can be performed under continuous visualization, including real-time images of the upper airway, glottic aperture and vocal cords with the camera 210 preferably positioned in the suction/camera channel, e.g., 20 or 120, and/or the ETT channel, e.g., 116 or 516.

The methods may further comprise connecting any of the laryngoscopes to an air/suction/vacuum source through the conduit (connector) and aspirating bodily secretions through the connector. The methods may further comprise keeping the airway accessible with the laryngoscope, and then positioning an endotracheal tube, e.g., the endotracheal tube 406 through the vocal cords by extending the distal end 406D of the endotracheal tube 406 from the distal end of the ETT channel. The placement of the endotracheal tube 406 can be conducted under continuous visualization by the camera 210 positioned preferably in the suction/camera channel. The placement can be guided with a bougie 208 positioned in the ETT channel. If it is necessary to aspirate body secretions at any time during any of these procedures, the laryngoscope can be connected to a suction/vacuum source through the suction connector and suction can take place without the need for inserting a separate suction catheter. Once the endotracheal tube 406 has been placed and its placement has been verified, the laryngoscope can be separated from the endotracheal tube 406 through the slit in the wall of the ETT channel. This separation step can be performed at the same time while the endotracheal tube 406 still remains positioned in place and providing ventilation to a patient.

In some embodiments of this disclosure, procedures can be conducted while the cuff 202 of the laryngoscope 200 is inflated. The laryngoscopes according to this disclosure can be used for various medical procedures, including, but are not limited to, conducting examination of an airway, gaining and maintaining access to an airway, assisting a patient with breathing, delivering a medication, and/or inserting an endotracheal tube.

In yet another aspect, the present disclosure provides methods for manufacturing the laryngoscopes according to this disclosure. The laryngoscope can be molded from one or more different plastic materials. In some embodiments, the handle and the blade can be made as two separate pieces which can be assembled together. In some embodiments, the handle may be attached detachably to the blade. The ETT channel, the suction/camera channel and any other channels, if present, can be designed in the mold and/or the channels can be extruded from the body of the laryngoscope. In some preferred embodiments, the laryngoscopes according to this disclosure can be disposable. Suitable cameras can be disposable or reusable.

From the foregoing description, all objections of the present invention are realized. A laryngoscope containing an ETT channel and/or suction/camera channel, systems comprising the laryngoscope, methods of their use, and manufacturing methods have been described. Certain additional embodiments may include the following.

Embodiment 1. A laryngoscope comprising a suction/camera channel, a handle and a blade with a proximal end and a distal end, the handle comprising a body with a distal end and a proximal end, the body being attached at the distal end to the proximal end of the blade, wherein the blade has a back surface and a front surface, wherein the laryngoscope contains at least one camera/suction entry port located on the body of the handle, the camera/suction entry port opening into the suction/camera channel located inside the body of the handle, the suction/camera channel opening with a camera/suction port on the back surface of the blade.

Embodiment 2. The laryngoscope of embodiment 1, wherein the handle is attached to the blade removably.

Embodiment 3. The laryngoscope of embodiment 1 or 2, wherein the suction/camera channel comprises a tube.

Embodiment 4. The laryngoscope of embodiment 1, 2 or 3, wherein the suction/camera channel comprises a tube which insertable into and removable from the body of the handle.

Embodiment 5. The laryngoscope of any one of embodiments 1-4, wherein the body of the handle further comprises a suction control port.

Embodiment 6. The laryngoscope of any one of embodiments 1-5, wherein the blade is curved.

Embodiment 7. The laryngoscope of any one of embodiments 1-6, wherein the laryngoscope further comprises a camera sheath insertable and removable from the suction/camera channel.

Embodiment 8. The laryngoscope of embodiment 7, wherein the camera sheath contains a sealed window at the distal end.

Embodiment 9. The laryngoscope of any one of embodiments 1-8, wherein the laryngoscope further comprises a camera/tool channel attached to the surface of the body of the handle and/or the camera/tool channel comprises a groove shaped in the surface of the body of the handle, wherein the camera/tool channel has a distal end and a proximal end, and wherein the distal end of the camera/tool channel opens on the back surface of the blade or on the side of the back surface of the blade, and wherein the proximal end of the camera/tool channel is positioned on the body of the handle.

Embodiment 10. The laryngoscope of any one of embodiments 1-9, wherein the camera/tool channel comprises a groove.

Embodiment 11. The laryngoscope of any one of embodiments 1-10, wherein the laryngoscope further comprises an adaptor attached to the camera/suction entry port.

Embodiment 12. The laryngoscope of any one of embodiments 1-11, wherein the body of the handle is substantially hollow.

Embodiment 13. The laryngoscope of any one of embodiments 1-12, wherein the laryngoscope further comprises a camera attached to a wand, the camera being insertable into and removable from the suction/camera channel.

Embodiment 14. An airway management device comprising the laryngoscope of any one of embodiments 1-13 and one or more of the following: at least one camera insertable and removable from the suction/camera channel, at least one bougie and/or at least one stopper for closing the camera/suction entry port.

Embodiment 15. A system for endotracheal intubation, the system comprising the laryngoscope according to any one of embodiments 1-13 attached to an air/vacuum/suction source and a camera inserted in the laryngoscope and capable of capturing images distally from the back surface of the blade.

Embodiment 16. A method for managing patient's airway, the method comprising inserting a camera in the camera/suction channel of the laryngoscope according to any one of embodiments 1-13, inserting a bougie into the camera/tool channel, inserting the blade into the oropharynx by manipulating the handle and with assistance from the bougie under continuous visualization by the camera.

Embodiment 17. The method of embodiment 16, wherein the method further comprises connecting the laryngoscope to an air/suction/vacuum source and establishing suction through the suction/camera channel and aspirating bodily secretions through the camera/suction port.

Embodiment 18. The method of embodiment 16 or 17, wherein suction is conducted under visualization by the camera.

Embodiment 19. The method of embodiment 16, 17 or 18, wherein the method further comprises opening and/or closing the suction control port.

What is claimed is:

1. A laryngoscope comprising a handle and a blade,
wherein the handle has a body with a proximal end and a distal end and having a length between the proximal end and the distal end,
wherein the blade is curved for lifting the epiglottis and gaining access to a subject's airway and sized to fit with the contour of a human larynx and wherein the blade has a distal end, a proximal end, a front surface, a back surface, a left flanking surface and a right flanking surface, and
wherein the handle is attached at its distal end to the proximal end of the blade at an angle, and
wherein the laryngoscope comprises an endotracheal tube (ETT) channel having a passageway encircled by a wall in the body of at least a portion of the handle length, wherein the ETT channel has a proximal end opening located at or near the proximal end of the handle and wherein the ETT channel has a distal end opening, and
wherein the laryngoscope further comprises a suction/camera channel having a dual function of performing suction while also housing a camera, the suction/camera channel being formed as a passageway in the body of the laryngoscope, wherein the suction/camera channel has a proximal end opening located at or near the proximal end of the handle and wherein the suction/camera channel has a distal end opening located at or near the distal end of the blade and wherein the suction/camera channel has a diameter compatible for positioning a camera in the suction/camera channel; and
wherein the laryngoscope further comprises a connector integrally formed to extend as a part of the body of the handle, the connector comprising a lumen enclosed by a wall attached to the body of the handle, the lumen opening into the suction/camera channel, wherein the connector is a port for connecting the suction/camera channel to an oxygen, suction and/or vacuum source.

2. The laryngoscope of claim 1, wherein the blade contains a protective flange extending distally from the distal end of the blade front surface and wherein the flange is distal to the distal end opening of the ETT channel.

3. The laryngoscope of claim 1, wherein the ETT channel contains a slit opening the ETT channel onto at least one surface of the laryngoscope.

4. The laryngoscope of claim 3, wherein the slit opens the ETT channel to the left flanking surface or to the right flanking surface of the laryngoscope.

5. The laryngoscope of claim 1, wherein the ETT channel opens with its distal end proximally to or at the distal end of the handle.

6. The laryngoscope of claim 1, wherein the ETT channel from the handle continues through at least a portion of the blade length and wherein the ETT channel opens with its distal end proximally to or at the distal end of the blade.

7. The laryngoscope of claim 1, wherein the laryngoscope comprises one or more guide grooves formed as a recess in at least a portion of the wall of the ETT channel and/or one or more guide grooves formed as a recess in one or more external surfaces of the handle and/or the blade, and wherein a depth of the guide groove is compatible with placing a bougie in the guide groove.

8. The laryngoscope of claim 1, wherein the laryngoscope further comprises a suction control port located on the handle, wherein the suction control port is a lumen in the body of the handle and wherein the lumen is connected to the suction/camera channel, and wherein the air pressure inside the suction/camera channel is controllable by opening and closing the suction control port.

9. The laryngoscope of claim 8, wherein the suction control port is located in a proximal portion of the front surface of the handle.

10. The laryngoscope of claim 8, wherein the suction control port is positioned on the front surface of the handle and proximally to the connector.

11. The laryngoscope of claim 1, wherein the laryngoscope further comprises a cuff attached to the distal portion of the blade, wherein the cuff is located proximally to the distal end of the blade, and wherein the distal end opening of the ETT channel and the distal end opening of the suction/camera channel are located distally to the cuff.

12. The laryngoscope of claim 11, wherein the cuff is inflatable and wherein the laryngoscope further contains a means for inflating the cuff.

13. The laryngoscope of claim 1, wherein the laryngoscope is J-shaped.

14. A system comprising the laryngoscope of claim 1, the system further comprising one or more of the following items:
 a) a camera adapter, wherein the camera adapter is a substantially cylindrical body enclosing a lumen for housing a camera;
 b) a channel adapter having a substantially conical body formed by a wall that encloses a lumen, the body having a distal end and a proximal end and a length between the distal end and a proximal end, wherein the conical body has a first diameter (d1) at the distal end and a second diameter (d2) at the proximal end, wherein the first diameter (d1) is smaller than the second diameter (d2), and wherein the first diameter (d1) is smaller than a diameter of the proximal end opening of the suction channel, and wherein the second diameter (d2) is larger than the diameter of the proximal end opening of the suction channel;

c) a bougie; and/or d) a camera.

15. An assembly comprising the laryngoscope of claim 1, a camera positioned in the suction/camera channel of the laryngoscope and an endotracheal tube positioned in the ETT channel of the laryngoscope.

16. A method for treating a patient, the method comprising placing a camera into the suction/camera channel of the laryngoscope according to claim 1 and introducing the assembly into patient's upper oral airway.

17. The method of claim 16, wherein the method further comprises manipulating the laryngoscope with assistance by a bougie positioned in a guide groove of the laryngoscope.

* * * * *